US007456270B2

(12) United States Patent
Mukerji et al.

(10) Patent No.: US 7,456,270 B2
(45) Date of Patent: Nov. 25, 2008

(54) Δ6-DESATURASE GENES AND USES THEREOF

(75) Inventors: Pradip Mukerji, Columbus, OH (US); Yung-Sheng Huang, Upper Arlington, OH (US); Amanda E. Leonard, Columbus, OH (US); Suzette L. Pereira, Westerville, OH (US); Jennifer M. Thurmond, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/931,626

(22) Filed: Sep. 1, 2004

(65) Prior Publication Data

US 2006/0048244 A1  Mar. 2, 2006

(51) Int. Cl.
*C07H 21/24* (2006.01)
*C12P 21/06* (2006.01)
*C12N 15/00* (2006.01)
*C12N 5/04* (2006.01)

(52) U.S. Cl. .................. 536/23.2; 435/69.1; 435/320.1; 435/419

(58) Field of Classification Search ........................ None
See application file for complete search history.

(56) References Cited

U.S. PATENT DOCUMENTS

| | | | |
|---|---|---|---|
| 4,582,788 A | 4/1986 | Erlich | |
| 4,666,701 A | 5/1987 | Horrobin et al. | |
| 4,683,194 A | 7/1987 | Saiki et al. | |
| 4,683,202 A | 7/1987 | Mullis | |
| 4,758,592 A | 7/1988 | Horrobin et al. | |
| 4,826,877 A | 5/1989 | Stewart et al. | |
| 4,943,674 A | 7/1990 | Houck et al. | |
| 4,945,050 A | 7/1990 | Sanford et al. | |
| 5,004,863 A | 4/1991 | Umbeck | |
| 5,106,739 A | 4/1992 | Comai et al. | |
| 5,107,065 A | 4/1992 | Shewmaker et al. | |
| 5,116,871 A | 5/1992 | Horrobin et al. | |
| 5,159,135 A | 10/1992 | Umbeck | |
| 5,175,095 A | 12/1992 | Martineau et al. | |
| 5,188,958 A | 2/1993 | Moloney et al. | |
| 5,231,020 A | 7/1993 | Jorgensen et al. | |
| 5,416,011 A | 5/1995 | Hinchee et al. | |
| 5,420,034 A | 5/1995 | Kridl et al. | |
| 5,443,974 A | 8/1995 | Hitz et al. | |
| 5,463,174 A | 10/1995 | Moloney et al. | |
| 5,518,908 A | 5/1996 | Corbin et al. | |
| 5,552,306 A | 9/1996 | Thomas et al. | |
| 5,569,834 A | 10/1996 | Hinchee et al. | |
| 5,589,379 A | 12/1996 | Kridl et al. | |
| 5,631,152 A | 5/1997 | Fry et al. | |
| 5,700,671 A | 12/1997 | Prieto et al. | |
| 5,750,176 A | 5/1998 | Prieto et al. | |
| 5,912,120 A | 6/1999 | Goldstein et al. | |
| 5,968,809 A * | 10/1999 | Knutzon et al. ........... | 435/254.2 |
| 6,340,705 B1 | 1/2002 | Obukowicz et al. | |
| 2002/0108147 A1 | 8/2002 | Thomas | |

FOREIGN PATENT DOCUMENTS

| | | |
|---|---|---|
| EP | 0050424 | 4/1982 |
| EP | 0084796 | 8/1983 |
| EP | 0201184 | 12/1986 |
| EP | 0237362 | 9/1987 |
| EP | 0258017 | 3/1988 |
| EP | 0304049 | 2/1989 |
| EP | 0843972 | 5/1998 |
| WO | 9311245 | 6/1993 |
| WO | 9411516 | 5/1994 |
| WO | 9524494 | 9/1995 |
| WO | 9613591 | 5/1996 |
| WO | 0020602 | 4/2000 |

OTHER PUBLICATIONS

Carninci et al., Genome Research, 2000, 10: 1617-1630.*
GENBANK Accession No. AK046961.*
Sakuradani et al., Gene, 1999, 238: 445-453.*
Abedinia, M., et al., "An Efficient Transformation System for the Australian Rice Cultivar, Jarrah", *Aust. J. Plant Physiol.*, 24:133-141 (1997).
Altschul, S.F., et al., "Gapped BLAST and PSI-BLAST: a new generation of protein database search programs", *Nucleic Acids Research*, 25(17):3389-3402 (1997).
Armstrong, C.L., et al., "Cell Biology & Molecular Genetics", *Crop Science*, 35:550-557 (1995).
Battraw, M. & Hall, T.C., "Expression of a chimeric neomycin phosphotransferase II gene in first and second generation transgenic rice plants", *Plant Science*, 86:191-202 (1992).
Birren, et al., Genome Analysis: Detecting Genes, vol. 1., 1-248 (1998).
Bower, R. & Birch, R.G., "Transgenic sugarcane plants via microprojectile bombardment", *The Plant Journ.*, 2(3):409-416 (1992).
Brenner, R.R., "Regulatory Function of Δ6 Desaturase—Key Enzyme of Polyunsaturated Fatty Acid Synthesis", *Adv. Exp. Med. Biol.*, 83:85-101 (1976).
Brutlag, D., "Computational Molecular Biology", http://cmgm.stanford.edu/biochem218/11Multiple.html, (2005).
Bytebier, B., et al., "T-DNA organization in tumor cultures and transgenic plants of the monocotyledon *Asparagus officinalis*", *Proc. Natl. Acad. Sci. USA*, 84:5345-5349 (1987).

(Continued)

*Primary Examiner*—Joseph Woitach
*Assistant Examiner*—Ileana Popa
(74) *Attorney, Agent, or Firm*—Sandra E. Weida; William J. Winter

(57) ABSTRACT

The subject invention relates to the identification of genes involved in the desaturation of polyunsaturated fatty acids at carbon 6 (i.e., "Δ6-desaturase"). In particular, Δ6-desaturase may be utilized, for example, in the conversion of linoleic acid to γ-linolenic acid and in the conversion of α-linolenic acid stearidonic acid. The polyunsaturated fatty acids produced by use of the enzyme may be added to pharmaceutical compositions, nutritional compositions, animal feeds, as well as other products such as cosmetics.

11 Claims, 7 Drawing Sheets

OTHER PUBLICATIONS

Grant, J.E., et al., "Transformation of peas (*Pisum sativum* L.) using immature cotyledons", *Plant Cell Rep.*, 15:953-657 (1996).

Cho, H.P., et al., "Identification of a Putative Mammalian Delta 6 Sesaturase (D6D) cDNA", *The FASEB Journ.*, Abstracts, Part 1:A532.

Christou, P., et al., "Stable Transformation of Soybean Callus by DNA-Coated Particles", *Plant Physiol.*, 87:671-674 (1988).

Christou, P., et al., "Production of Transgenic Rice (*Oryza Sativa L.*) Plants from Agronomically Important Indica and Japonica Varieties Via Electric Discharge Particle Acceleration of Exogenous DNA into Immature Zygotic Embryos", *Bio/Technology*, 9:957-962 (1991).

DeAlmeida, E.R.P., et al., "Transgenic expresion of two marker genes under the control of an *Arabidopsis rbcS* promoter: Sequences encoding the Rubisco transit peptide increase expression levels", *Mol. Gen. Genetics*, 218:78-86 (1989).

De la Peña, A., et al., "Transgenic rye plants obtained by injecting DNA into young floral tillers", *Nature*, 325:274-276 (1987).

Fromm, M.E., et al., "Inheritance and Expression of Chimeric Genes in the Progeny of Transgenic Maize Plants", *Bio/Technology*, 8:833-839 (1990).

Goff, S.A., et al., "Transactivation of anthocyanin biosynthetic genes following transfer of *B* regulatory genes into maize tissues", *The EMBO Journ.*, 9(8):2517-2522 (1990).

Gofdon-Kamm, et al., "Transformation of Maize Cells and Regeneration of Fertile Transgenic Plants", *The Plant Cell*, 2:603-618 (1990).

Grant, et al.,.

Hattori, T., et al., "The *Viviparous-1*gene and abscisic acid activate the *C1*regulatory gene for anthocyanin biosynthesis during seed maturation in maize", *Genes & Dev.*, 6:609-618 (1992).

Higgins, D.G. & Sharp, P.M., "Fast and sensitive multiple sequence alignments on a microcomputer", *CABIOS*, 5(2):151-153 (2000).

Horn, M.E., et al., "Transgenic plants of Orchardgrass (*Dactylis glomerata.*) from protoplasts", *Plant Cell Rep.*, 7:469-472 (1988).

Horrobin, D.V., "Fatty acid metabolism in health and disease: the role of Δ-6-desaturase", *Am. J. Clin. Nutri.*, 57(suppl):732S-737S (1993).

Ingelbrecht, I.L.W., et al., "Different 3' End Regions Strongly Influence the Level of Gene Expression in Plant Cells", *The Plant Cell*, 1:671-680 (1989).

Ishida, Y., et al., "High efficiency transformation of maize (*Zea mays* L.) mediated by *Agrobacterium tumefaciens*", *Nature Biotech.*, 14:745-750 (1996).

Jones, J.D.G., et al., "High level expression of introduced chimaeric genes in regenerated transformed plants", *The EMBO Journ.*, 4(10):2411-2418 (1985).

Klein, T.M., et al., "High-velocity microprojectiles for delivering nucleic acids into living cells", *Nature*, 327:70-73 (1987).

Koziel, M.G., et al., "Field Performance of Elite Transgenic Maize Plants Expressing an Insecticidal IProtein Derived from *Baillus thuringiensis*", *Bio/Technology*, 11:194-200 (1993).

Maliga, P., et al., "Methods in Plant Molecular Biology-A Laboratory Course Manual", *Cold Spring Harbor Laboratory Press*, (1995).

Marcotte, Jr., W.R., et al., "Regulation of a wheat promoter by abscisic acid in rice protoplasts", *Nature*, 335:454-457 (1988).

McCabe, D.E., et al., "Stable Transformation of Soybean (*Glycine Max*) by Particle Acceleration", *Bio/Technology*, 6:923-926 (1988).

McCarty, D.R., et al., "Molecular Analysis of *viviparous*-1: An Abscisic Acid-Insensitive Mutant of Maize", *The Plant Cell*, 1:523-532 (1989).

McCarty, D.R., et al., "The *Viviparous-1* Developmental Gene of Maize Encodes a Novel Transcriptional Activator", *Cell*, 66:895-905 (1991).

McKently, A.H., et al., "*Agrobacteium*-mediated transformation of peanut (*Arachis hypogaea* L.) embryo axes and the development of transgenic plants", *Plant Cell Reports*, 14:699-703 (1995).

Mullis, K., et al., "Specific Enzymatic Amplification of DNA in Vitro: The Polymerase Chain Reaction", *Cold Spring Harbor Symp. Quant. Biol.*, 51:263-273 (1986).

Needleman, S.B. & Wunsch, C.D., "A General Method Applicable to the Search for Similarities in the Amino Acid Sequence of Two Proteins", *J. Mol. Biol.*, 48:443-453 (1970).

Okamuro, J.K. & Goldberg, R.B., "Regulation of Plant Gene Expression: General Principles", *Biochem of Plants*, 15:1-82 (1989).

Park, S.H., "T-DNA integration into genomic DNS of rice following *Agrobactrium* inoculation of isolated shoot apices", *Plant Mol. Biol.*, 32:1135-1148 (1996).

Pearson, W.R. & Lipman, D.J., "Improved tools for biological sequence comparison", *Proc. Natl. Acad. Sci. USA*, 85:2444-2448 (1988).

Rhodes, C.A., et al., "Genetically Transformed Maize Plants from Protoplasts", *Science*, 240:204-207 (1988).

Sambrook, J., et al., *Molecular Cloning—A Laboratory Manual*, $2^{nd}$ Ed., 1989.

Schnieke, A. E., et al., "Human Factor IX Transgenic Sheep Produced by Transfer of Nuclei from Transfected Fetal Fibroblasts", *Science*, 278:2130-2133 (1997).

Smith, T.F. & Watrman, M.S., "Comparison of Biosequences", *Appl. Math.*, 2:482-489 (1981).

Somers, D.A., et al., Fertile, Transgenic Oat Plants, *Bio/Technology*, 10:1589-1594 (1992).

Tijssen, P., "Overview of principles of hybridization and the strategy of nucleic acid probe assays", *Laboratory Techniques in Biochemistry and Molecular Biology*, 24:19-78 (1993).

Toriyama, K., et al., "Haploid and diplois plant regeneration from protoplasts of anther callus in rice", *Theor. Appl. Genet.*, 73:16-19 (1986).

Turner, R. & Foster, G.D., "The Potential Exploitation of Plant Viral Translational Enhancers in Biotechnology for Increased Gene Expression", *Mol. Biotech.*, 3:225-236 (1995).

Vasil, V., et al., "Herbicide Resistant Fertile Transgenic Wheat Plants Obtained by Microprojectile Bombardment of Regenerable Embryogenic Callus", *Bio/Technology*, 10:667-674 (1992).

Wan, Y. & Lemaux, P.G., "Generation of Large Numbers of Independently Transformed Fertile Barley Plants", *Plant Physiol.*, 104:37-48 (1994).

Wang, Z-yu, et al., "Transgenic Plants of Tall Fescue (*Festuca Arundinacea* Schreb.) Ovbtained by Direct Gene Transfer to Protoplasts", *Bio/Technology*, 10:691-696 (1992).

Weissbach, A. & Weissbach H., "Methods for Plant Molecular Biology", *Academic Press*, San Diego, CA, (1988).

Zhang, H.M., et al., "Transgenic rice plants produced by electroporation-mediated plasmid uptake into protoplasts", *Plant Cell Rep.*, 7:379-384 (1988).

Zhang, W. & Wu, R., "Efficient regeneration of transgenic plants from rice protoplasts and correctly regulated expression of the foreign gene in the plants", *Theor. Appl. Genet.*, 76:835-840 (1988).

Huang, Y.S., "Cloning of delta12- and delta6-desaturases from *Mortierella alpina* and recombinant production of gamma-linolenic acid in *Saccaromuces cerevisiae*", *Genbank*, Accession AF110510 (1999).

Pereira, S.L. et al., "Recent Advances in the Study of Fatty Acid Desaturases from Animals and Lower Eukaryotes", *Prostaglandins Leukotrienes and Essential Fatty Acids—Churchill Livingstone Medical Journal.*, 68(2):97-106 (2003).

Chen Hung-Chang et al., "Screening of Microbes for the Production of Polyunsaturated Fatty Acids", *Journal of the Chinese Agricultural Chemical Society*, 32(1):33-46 (1994).

\* cited by examiner

GAP alignment of translated amino acid sequence in Figure 3 and
the *Mortierella alpina* Δ6-desaturase.

```
     Gap Weight:        8       Average Match:     2.778
  Length Weight:        2       Average Mismatch: -2.248
       Quality:     1021                Length:     462
         Ratio:    2.844                  Gaps:       4
Percent Similarity: 61.972    Percent Identity: 53.521
    Match display thresholds for the alignment(s):
                  | = IDENTITY
                  : = 2
                  . = 1
```

Delacroixia-consensus.pep x MalpinaD6.pep

```
  1 ........................................VYDVTEWVKRH 11
                                             |||| |.| |
  1 MAAAPSVRTFTRAEILNAEALNEGKKDAEAPFLMIIDNKVYDVREFVPDH 50

12 PGGPIILTHVGRDGTDAFHTFHPDSSWETLANYYVGDIHPDD.VINQDSK 60
    ||| :||||||:|||| | |||:..||||||:|||| |   |   |
 51 PGGSVILTHVGKDGTDVFDTFHPEAAWETLANFYVGDIDESDRAIKND.. 98

61 PSFLTDIRKLKDKYYKLGYFNADMGFYTYKCLSTVSIFALSVTILYNF.S 109
    |  ::|||:  :  |||:..   :|:|    .|. ||  |.
 99 .DFAAEVRKLRTLFQSLGYYDSSKAYYAFKVSFNLCIWGLSTFIVAKWGQ 147

110 SSWFGIIPSAMIMGLFWQQCGWLSHDFLHHQVSDNRDINNAIGGLFYGAV 159
     .|   :  || ::||||||||||.||||||   .|.    |   | ||
148 TSTLANVLSAALLGLFWQQCGWLAHDFLHHQVFQDRFWGDLFGA.FLGGV 196

160 CQGFSMSWWKDKHNTHHAAPNVYNEDPDIDTHPFLAWSEQAMELYADLND 209
    |||||  |||||||||||||||| :|||||||||| | ||| |:|::.|.|
197 CQGFSSSWWKDKHNTHHAAPNVHGEDPDIDTHPLLTWSEHALEMFSDVPD 246

210 QEMSSRMKKFMLTNQAIIYFPLLTFARLSWCTYSLWFCFSRGTLSNPNKI 259
    :|:.   :||. ||   |||:|.||||||||  |: |   |    |.
247 EELTRMWSRFMVLNQTWFYFPILSFARLSWCLQSIMFVLPNGQAIIKPSGA 296

260 PINIEFSEKAALLTHWFITLSITVFMPSTWIQSLVFFIVCQASCGVLLAS 309
    : |  |. .| ||  |.    : :|:|:| || ||| |||
297 RVPISLVEQLSLAMHWTWYLATMFLFIKDPVNMIVYFLVSQAVCGNLLAT 346

310 VFSLNHNGMAVISTEEADNMDFYTKQVITGRDVTPSHFIQWFCGGLNYQI 359
    ||||||||| ||| |||  .|||:|||:|||: | | || ||||||||
347 VFSLNHNGMPVISKEEAVDMDFFTKQII GRDVHPGLFANWFTGGLNYQI 396
```

FIG. 2

Comparison of the location of the various 'ATG' start codons (bold, underlined) created in the putative desaturase gene sequence (Del-D6) from Delacroixia.

Consensus: M N G N K I * A I K E G A I L T F I L I G G V......

pRDC8:     <u>M</u> N G N K I <u>A</u> A I K E G A I L T F I L I G G V......

pRDC10:                <u>M</u> A I K E G A I L T F I L I G G V......

pRDC12:                                    <u>M</u> L I G G V......

FIG. 3

Alignment of the putative amino acid sequences encoded by Del-D6 (in pRDC12), the Δ6-desaturase from *Delacroixia coronatus* ATCC 28565, and the *Mortierella alpina* Δ6-desaturase

```
    Gap Weight:         8      Average Match:     2.778
 Length Weight:         2      Average Mismatch: -2.248

Quality:      1231              Length:     464
         Ratio:     2.700                Gaps:       6
Percent Similarity: 60.444     Percent Identity: 51.333

Match display thresholds for the alignment(s):
                  | = IDENTITY
                  : = 2
                  . = 1
```

Del-D6.pep x MalpinaD6.pep

```
  1 .MLIGGVKLFRRSE.LNTHTSSKDILTSKVYAPAYTIIDNKVYDVRDFIL 48
     |: | |.| ||     ..         ||   ||||||||||:|:
  1 MAAAPSVRTFTRAEILNAEALNEG..KKDAEAPFLMIIDNKVYDVREFVP 48

49 DHPGGPIILTHVGRDGTDAFHTFHPDSSWETLANYYVGDIHPDD.VINQD 97
    ||||| :||||||:|||| | ||||:...||||||:|||||   | | |
 49 DHPGGSVILTHVGKDGTDVFDTFHPEAAWETLANFYVGDIDESDRAIKND 98

98 SKPSFLTDIRKLKDKYYKLGYFNADMGFYTYKCLSTVSIFALSVTILYNF 147
      |  ::|||:  :  |||:..    :| :|   .|. ||  |. .
 99 ...DFAAEVRKLRTLFQSLGYYDSSKAYYAFKVSFNLCIWGLSTFIVAKW 145
```

FIG. 4A

```
148 .SSSWFGIIPSAMIMGLFWQQCGWLSHDFLHHQVSDNRDINNAIGGLFYG 196
     .|   :  ||  :: ||||||||||.|||||||||  .|   .   |  | |
146 GQTSTLANVLSAALLGLFWQQCGWLAHDFLHHQVFQDRFWGDLFGA.FLG 194

197 AVCQGFSMSWWKDKHNTHHAAPNVYNEDPDIDTHPFLAWSEQAMELYADL 246
    ||||||  |||||||||||||||||: |||||||||  |  ||| |:|::.|.
195 GVCQGFSSSWWKDKHNTHHAAPNVHGEDPDIDTHPLLTWSEHALEMFSDV 244

247 NDQEMSSRMKKFMLTNQAIIYFPLLTFARLSWCTYSLWFCFSRGTLSNPN 296
    |:|:.    :||. ||   |||:|.||||||| |: |    |     |.
245 PDEELTRMWSRFMVLNQTWFYFPILSFARLSWCLQSIMFVLPNGQAHKPS 294

297 KIPINIEFSEKAALLTHWFITLSITVFMPSTWIQSLVFFIVCQASCGVLL 346
     : |   |. .| ||  |.             :   :|:|:| || || ||
295 GARVPISLVEQLSLAMHWTWYLATMFLFIKDPVNMIVYFLVSQAVCGNLL 344

347 ASVFSLNHNGMAVISTEEADNMDFYTKQVITGRDVTPSHFIQWFCGGLNY 396
    | |||||||| ||| ||| |||.|||:|||:||||| |  | ||  |||||
345 AIVFSLNHNGMPVISKEEAVDMDFFTKQIITGRDVHPGLFANWFTGGLNY 394

397 QVEHHLFPALPRHSLPKVQADIEALCKKHGIPYHMTGFIDGTKEVLDRLQ 446
    |:||||||.:|||. |:|  :| ||||:|: || || |:|| ||  ||
395 QIEHHLFPSMPRHNFSKIQPAVETLCKKYGVRYHTTGMIEGTAEVFSRLN 444

447 KIATNINDQI.... 456
     .:.       .
445 EVSKAASKMGKAQ* 458
```

FIG. 4B

```
                              1                                                            60
Delacroxia-D6    (1)  --MLIGGVKLFRRSELNTHTSSKDILTSKVYAPAYTIIDNKVYDVRDFILDHPCGP-IIL
   M. alpina-D6  (1)  -MAAAPSVRTFTRAEILNAEALNE-GKKDAEAPFLMIIDNKVYDVREFVPDHPGGS-VIL
        Phaeo-D6 (1)  -MGKGGDARASKGSTAARKISWQEVKTHASPEDAWIIHSNKVYDVSNW-HEHPGGA-VIF
      Rhizopus-D6(1)  -MSTSDRQSVFTLKELELINQKHR--DGDKSAMKFIIIDRKVYDVTEFLEDHPGGAQVLL
       Pythium-D6(1)  --------MVDLKPGVKRLVSWKEIREHATPATAWIVIHHKVYDISKW-DSHPGGS-VML
         Mucor-D6(1)  MSSDVGATVPHFYTRAELADIHQDVLDKKPEARKLIVVENKVYDITDFVFDHPGGERVLL 61                                                           120
Delacroxia-D6   (58)  THVGRDGTDAFHTFHPDSSWETLANYYVGDIHPDDVINQDSKPS--------------FLT
   M. alpina-D6 (58)  THVGKDGTDVFDTFHPEAAWETLANFYVGDIDESDRAIKNDD---------------FAA
        Phaeo-D6(58)  THAGDDMTDIFAAFHAPGSQSLMKKFYIGELLPETTGKEPQQ---------------IAFEK
      Rhizopus-D6(58) THVGKDASDVFHAMHPESAYEILNNYFVGDVKDAHVKETPSAQ--------------FAS
       Pythium-D6(51) TQAGEDATDAFAVFHPSSALKLLEQFYVGDVDETSKAEIEGEPASDEERARRERINEFIA
         Mucor-D6(61) TQEGRDATDVFHEMHPPSAYELLANCYVGDCEPKLPIDSTDKKALNSA--------AFAQ 121                                                           180
Delacroxia-D6  (105)  DIRKLKDKYYKLGYFNADMGFYTYKCLSTVSIFALSVTILYNF-SSSWFGIIPSAMIMGL
   M. alpina-D6(103)  EVRKLRTLFQSLGYYDSSKAYYAFKVSFNLCIWGLSTFIVAKWGQTSTLANVLSAALLGL
        Phaeo-D6(105) GYRDLRSKLIMMGMFKSNKWFYVYKCLSNMAIWAAACALVFYS--DRFWVHLASAVMLGT
      Rhizopus-D6(104) EMRQLRDQLKKEGYFHSSKAYYVYKVLSTLALCAAGLTLLYAYGHTSTLAVVASAIIVGI
       Pythium-D6(111) SYRRLRVKVKGMGLYDASALYYAWKLVSTFGIAVLSMAICFFF--NSFAMYMVAGVIMGL
         Mucor-D6(113) EIRDLRDKLEKQGYFDASTGFYIYKVSTTLLVCIVGLAILKAWGRESTLAVFIAASLVGL 181                                                           240
Delacroxia-D6  (164)  FWQQCGWLSHDFLHHQVSDNRDINNAIGGLFYGAVCQGFSMSWWKDKHNTHHAAPNVYNE
   M. alpina-D6(163)  FWQQCGWLAHDFLHHQVFQDRFWCDLFG-AFLGGVCQGFSSSWWKDKHNTHHAAPNVHGE
        Phaeo-D6(163) FFQQSGWLAHDFLHHQVFTKRKHGDLGG-LFWGNLMQCYSVQWWKNKHNGHHAVPNLHCS
      Rhizopus-D6(164) FWQQCGWLAHDFGHHQCFEDRSWNDVLV-VFLGNFCQGFSLSWWKNKHNTHHASTNVHGH
       Pythium-D6(169) FYQQSGWLAHDFLHNQVCENRTLGNLIG-CLVGNAWQGFSVQWWKNKHNLHHAVPNLHSA
         Mucor-D6(173) FWQQCGWLAHDYAHQVIKDPNVNNLFL-VTFGNLVQGFSLSWWKNKHNTHHASTNVSGE
```

FIG. 5A

```
                        241                                                         300
Delacroxia-D6  (224) -------DPDIDTHPFLAWS-EQAMELYADLNDQE----MSSRMKKFMLTNQAIIYFPLLT
   M. alpina-D6 (222) -------DPDIDTHPLLTWS-EHALEMFSDVPDEE----LTRMWSRFMVLNQTWFYFPILS
       Phaeo-D6 (222) SAVAQDGDPDIDTMPLLAWSVQQAQSYRELQADGK----DSGLVKFMIRNQSYFYFPILL
    Rhizopus-D6 (223) -------DPDIDTAPVLLWD-EYASAAYYASLDEEPTMISRFLAESVLPHQTRYYFFVLG
     Pythium-D6 (228) KDEGFIGDPDIDTMPLLAWSKEMARKAFESAHGP-----------FFIRNQAFLYFPLLL
       Mucor-D6 (232) -------DPDIDTAPILLWD-EFAVANFYGSLKDNASGFDRFIAEHILPYQTRYYFFILG 301                                                         360
Delacroxia-D6  (273) FARLSWCTYSLWFCFSRGTLSNPNKIPI------NIEFSEKAALLTHWFITLSITV-FMPS
   M. alpina-D6 (271) FARLSWCLQSIMFVLPNGQAHKPSGARV-----PISLVEQLSLAMHWTWYLATMF-LFIK
       Phaeo-D6 (278) LARLSWLNESFKCAFGLGAASENAALELKAKGLQYPLLEKAGILLHYAWMLTVSSGFGRF
    Rhizopus-D6 (275) FARLSWAIQSLLYSFKQGAINKSH---------QLNLFERFCLVSHWTLFTYCTL-AWCS
     Pythium-D6 (277) LARLSWLAQSFFYVFTEFSFGIFDK--V------EFDGPEKAGLIVHYIWQLAIPY-FCNM
       Mucor-D6 (284) FARTSWAIQSIIYSFKNETLNKSK----------LLSWCERIFLIVHWVFFTYCTI-AWIS 361                                                         420
Delacroxia-D6  (327) TWIQSLVFFIVCQASCGVLLASVFSLNHNGMAVISTEEADNMDFYTKQVITGRDVT----
   M. alpina-D6 (325) DPVNMIVYFLVSQAVCGNLLAIVFSLNHNGMPVISKEEAVDMDFFTKQIITGRDVH----
       Phaeo-D6 (338) SFAYTAFYFLTATASCGFLLAIVFGLGHNGMATYNADARP--DFWKLQVTTTRNVTGGHG
    Rhizopus-D6 (325) NVYHMILFFLVSQATTGYTLALVFALNHNGMPVITEEKAESMEFFEIQVITGRDVT----
     Pythium-D6 (329) SLFEGVAYFLMGQASCGLLLALVFSIGHNGMSVYERETKP--DFWQLQVTTTRNIR----
       Mucor-D6 (334) SIRNIAMFFVVSQITTGYLLAIVFAMNHNGMPVYSPEEANHTEFYELQCITGRDVN----

421                                                         480
Delacroxia-D6  (383) -PSHFIQWFCGGLNYQVEHHLFPALPRHSLPKVQADIEALCKKHGIPYHMTGFIDGTKEV
   M. alpina-D6 (381) -PGLFANWFTGGLNYQIEHHLFPSMPRHNFSKIQPAVETLCKKYGVRYHTTGMIEGTAEV
       Phaeo-D6 (396) FPQAFVDWFCGGLQYQVDHHLFPSLPRHNLAKTHALVESFCKEWGVQYHEADLVDGTMEV
    Rhizopus-D6 (381) -LSPLGDWFMGGLNYQIEHHVFPNMPRHNLPKVKPMVKSLCKKYDINYHDTGFLKGTLEV
     Pythium-D6 (383) -ASVFMDWFTGGLNYQIDHHLFPLVPRHNLPKVNVLIKSLCKEFDIPFHETGFWEGIYEV
       Mucor-D6 (390)  CTVFGDWLMGGLNYQIEHHLFPEMPRHLSKVKSMVKPIAQKYNIPYHDTTVIGGTIEV 481       502
Delacroxia-D6  (442) LDRLQKIATNINDQI-------
   M. alpina-D6 (440) FSRLNEVSKAASKMGKAQ----
       Phaeo-D6 (456) LHHLGSVAGEFVVDFVRDGPAM
    Rhizopus-D6 (440) LKTLDITSKLSLQLSKKSF---
     Pythium-D6 (442) VDHLADISKEFITEFPAM----
       Mucor-D6 (449) LQTLDFVQKISQKFSKKML---
```

Δ6-DESATURASE GENES AND USES THEREOF

BACKGROUND OF THE INVENTION

1. Technical Field

The subject invention relates to the identification and isolation of genes that encode an enzyme (i.e., Δ6-desaturase) involved in the synthesis of polyunsaturated fatty acids and to uses thereof. In particular, Δ6-desaturase catalyzes the conversion of, for example, linoleic acid (C18:2n-6) to γ-linolenic acid (C18:3n-6) and α-linolenic acid (C18:3n-3) to stearidonic acid (C18:4n-3). The converted products may then be utilized as substrates in the production of other polyunsaturated fatty acids (PUFAs). The products or other polyunsaturated fatty acids may be added to pharmaceutical compositions, nutritional compositions, animal feeds as well as other products such as cosmetics.

2. Background Information

Desaturases are critical in the production of long-chain polyunsaturated fatty acids that have many important functions. For example, polyunsaturated fatty acids (PUFAs) are important components of the plasma membrane of a cell, where they are found in the form of phospholipids. They also serve as precursors to mammalian prostacyclins, eicosanoids, leukotrienes and prostaglandins.

Additionally, PUFAs are necessary for the proper development of the developing infant brain as well as for tissue formation and repair. In view of the biological significance of PUFAs, attempts are being made to produce them, as well as intermediates leading to their production, in an efficient manner.

A number of enzymes, most notably desaturases and elongases, are involved in PUFA biosynthesis (see FIG. 1). For example, an elongase (elo) catalyzes the conversion of γ-linolenic acid (GLA) to dihomo-γ-linolenic acid (DGLA) and of stearidonic acid (C18:4n-3) to (n-3)-eicosatetraenoic acid (C20:4n-3). Linoleic acid (LA, C18:2n-9, 12 or C18:2n-6) is produced from oleic acid (C18:1-Δ9) by a Δ12-desaturase. GLA (C18:3n-6, 9, 12) is produced from linoleic acid by a Δ6-desaturase.

It must be noted that animals cannot desaturate beyond the Δ9 position and therefore cannot convert oleic acid into linoleic acid. Likewise, γ-linolenic acid (ALA, C18:3n-9, 12, 15) cannot be synthesized by mammals. However, γ-linolenic acid can be converted to stearidonic acid (STA, C18:4n-6, 9, 12, 15) by a Δ6-desaturase (see PCT publication WO 96/13591 and *The FASEB Journal*, Abstracts, Part I, Abstract 3093, page A532 (Experimental Biology 98, San Francisco, Calif., Apr. 18-22, 1998); see also U.S. Pat. No. 5,552,306), followed by elongation to (n-3)-eicosatetraenoic acid (C20: 4n-8, 11, 14, 17) in mammals and algae. This polyunsaturated fatty acid (i.e., C20:4n-8, 11, 14, 17) can then be converted to eicosapentaenoic acid (EPA, C20:5n-5, 8, 11, 14, 17) by a Δ5-desaturase. EPA can then, in turn, be converted to ω3-docosapentaenoic acid (C22:5n-3) by an elongase.

Other eukaryotes, including fungi and plants, have enzymes which desaturate at carbon 12 (see PCT publication WO 94/11516 and U.S. Pat. No. 5,443,974) and carbon 15 (see PCT publication WO 93/11245). The major polyunsaturated fatty acids of animals therefore are either derived from diet and/or from desaturation and elongation of linoleic acid or γ-linolenic acid. In view of these difficulties, it is of significant interest to isolate genes involved in PUFA synthesis from species that naturally produce these fatty acids and to express these genes in a microbial, plant, or animal system which can be altered to provide production of commercial quantities of one or more PUFAs.

In view of the above discussion, there is a definite need for the Δ6-desaturase enzyme, the respective genes encoding this enzyme, as well as recombinant methods of producing this enzyme. Additionally, a need exists for oils containing levels of PUFAs beyond those naturally present as well as those enriched in novel PUFAs. Such oils can only be made by isolation and expression of the Δ6-desaturase genes.

All U.S. patents and publications referred to herein are hereby incorporated in their entirety by reference.

SUMMARY OF THE INVENTION

The present invention includes an isolated nucleotide sequence or fragment thereof encoding a polypeptide having desaturase activity, wherein said polypeptide comprises an amino acid sequence having at least 90% amino acid sequence identity to an amino acid sequence selected from the group consisting of SEQ ID NO:2, SEQ ID NO:4, SEQ ID NO:6 and SEQ ID NO:8.

Additionally, the present invention encompasses an isolated nucleic acid sequence or fragment thereof comprising, or complementary to, a nucleotide sequence having at least 90% nucleotide sequence identity to a nucleotide sequence selected from the group consisting of SEQ ID NO:1, SEQ ID NO:3, SEQ ID NO:5 and SEQ ID NO:7.

The nucleotide sequences described above encode a functionally active desaturase that utilizes a monounsaturated or polyunsaturated fatty acid as a substrate. The nucleotide sequences may be derived for example, from *Delacroixia coronatus*. The present invention also includes purified proteins and fragments thereof encoded by the above-referenced nucleotide sequences.

In particular, the present invention also includes a purified polypeptide which desaturates polyunsaturated fatty acids at carbon 6 and has an amino acid sequence having at least 90% amino acid identity to an amino acid sequence selected from the group consisting of SEQ ID NO:2, SEQ ID NO:4, SEQ ID NO:6 and SEQ ID NO:8.

Additionally, the present invention includes a method of producing a desaturase comprising the steps of: isolating a nucleotide sequence comprising or complementary to a nucleotide sequence encoding a polypeptide comprising an amino acid sequence having at least 90% identity to an amino acid sequence of SEQ ID NO:2, SEQ ID NO:4, SEQ ID NO:6 and SEQ ID NO:8; constructing a vector comprising: i) the isolated nucleotide sequence operably linked to ii) a promoter; and introducing said vector into a host cell for a time and under conditions sufficient for expression of the desaturase. The host cell may be, for example, a eukaryotic cell or a prokaryotic cell. In particular, the prokaryotic cell may be, for example, *E. coli*, cyanobacteria or *B. subtilis*. The eukaryotic cell may be, for example, a mammalian cell, an insect cell, a plant cell or a fungal cell (e.g., a yeast cell such as *Saccharomyces cerevisiae*, *Saccharomyces carlsbergensis*, *Candida* spp., *Lipomyces starkey*, *Yarrowia lipolytica*, *Kluyveromyces* spp., *Hansenula* spp., *Trichoderma* spp. or *Pichia* spp.). Other fungal hosts such as *Rizopus* spp., *Aspergillus* spp. and *Mucor* spp. may also be utilized.

Moreover, the present invention also includes a vector comprising: an isolated nucleotide sequence comprising or complementary to a nucleotide sequence encoding a polypeptide having an amino acid sequence having at least 90% amino acid identity to an amino acid sequence selected from the group consisting of SEQ ID NO:2, SEQ ID NO:4, SEQ ID NO:6 and SEQ ID NO:8, operably linked to a regulatory sequence (e.g., a promoter). The invention also includes a host cell comprising this vector. The host cell may be, for example, a eukaryotic cell or a prokaryotic cell. Suitable eukaryotic cells and prokaryotic cells are as defined above.

Additionally, the present invention includes an isolated plant cell, plant or plant tissue comprising the above vector, wherein expression of the nucleotide sequence of the vector results in production of a polyunsaturated fatty acid by the plant cell, plant or plant tissue. The polyunsaturated fatty acid may be, for example, selected from the group consisting of γ-linolenic acid or stearidonic acid. The invention also includes one or more plant oils or acids expressed by the above plant cell, plant or plant tissue.

Additionally, the present invention also encompasses a transgenic plant comprising the above vector, wherein expression of the nucleotide sequence of the vector results in production of a polyunsaturated fatty acid in seeds of the transgenic plant.

The present invention also includes a method ("first method") for producing a polyunsaturated fatty acid comprising the steps of: isolating a nucleic acid sequence comprising or complementary to a nucleotide sequence encoding a polypeptide comprising an amino acid sequence having at least 90% amino acid sequence identity to an amino acid sequence selected from the group consisting of SEQ ID NO:2, SEQ ID NO:4, SEQ ID NO:6 and SEQ ID NO:8 or 90% nucleotide sequence identity to a nucleotide sequence selected from the group consisting of SEQ ID NO:1, SEQ ID NO:3, SEQ ID NO:5 and SEQ ID NO:7; constructing a vector comprising the isolated nucleotide sequence; introducing the vector into a host cell for a time and under conditions sufficient for expression of Δ6-desaturase; and exposing the expressed Δ6-desaturase to a substrate polyunsaturated fatty acid in order to convert the substrate to a product polyunsaturated fatty acid. The substrate polyunsaturated fatty acid may be, for example, linolenic acid or α-linolenic acid, and the product polyunsaturated fatty acid may be, for example, γ-linolenic acid or stearidonic acid, respectively. This method may further comprise the step of exposing the product polyunsaturated fatty acid to another enzyme (e.g., an elongase) in order to convert the product polyunsaturated fatty acid to another polyunsaturated fatty acid (i.e., "second" method). In this method containing the additional step (i.e., "second" method), the product polyunsaturated fatty acid may be, for example, γ-linolenic acid or stearidonic acid and the "another" polyunsaturated fatty acid may be, for example, dihomo-γ-linolenic acid or eicosatetraenoic acid.

Also, the present invention includes a method of producing a polyunsaturated fatty acid comprising the steps of: exposing a substrate monounsaturated or polyunsaturated fatty acid to an enzyme (e.g., an elongase or desaturase) in order to convert the substrate to a product polyunsaturated fatty acid; and exposing the product polyunsaturated fatty acid to a Δ6-desaturase comprising the amino acid sequence selected from the group consisting of SEQ ID NO:2, SEQ ID NO:4, SEQ ID NO:6 and SEQ ID NO:8, in order to convert the product polyunsaturated fatty acid to a final product polyunsaturated fatty acid.

For example, a substrate polyunsaturated fatty acid (e.g., linoleic acid) may be exposed to a ω3-desaturase (e.g., Δ15-desaturase) in order to convert the substrate to a "product" polyunsaturated fatty acid (e.g., α-linolenic acid). The product polyunsaturated fatty acid may then be converted to a "final" product polyunsaturated fatty acid (e.g., stearidonic acid) by exposure to the Δ6-desaturase of the present invention (see FIG. 1). Alternatively, a substrate monounsaturated fatty acid such as oleic acid may be exposed to a desaturase (e.g., Δ12-desaturase) in order to convert the substrate to a product polyunsaturated fatty acid such as linoleic acid. The product polyunsaturated fatty acid may then be converted to the final product polyunsaturated fatty acid, γ-linolenic acid by exposure to the Δ6-desaturase of the present invention. Thus, the Δ6-desaturase is utilized in the last step of the method in order to create the "final" desired product. As another example, one may expose linoleic acid to a Δ6-desaturase in order to create γ-linolenic acid (GLA), and then expose the GLA to an elongase to create dihomo-γ-linolenic acid (DGLA) and then expose DGLA to a Δ5-desaturase in order to create arachidonic acid (AA). The AA may then be exposed to an elongase in order to convert it to adrenic acid. Finally, the adrenic acid may be exposed to Δ4-desaturase in order to convert it to ω6-docosapentaenoic acid (see FIG. 1). Thus, the method involves the utilization of a linoleic acid substrate and a series of desaturase and elongase enzymes, in addition to the Δ6-desaturase, in order to arrive at the final product. (Possible substrates include those shown in FIG. 1, for example, linoleic acid and α-linolenic acid.)

The present invention also encompasses a composition comprising at least one polyunsaturated fatty acid selected from the group consisting of the "product" polyunsaturated fatty acid produced according to the methods described above and the "another" polyunsaturated fatty acid produced according to the methods described above. The product polyunsaturated fatty acid may be, for example, γ-linolenic acid or stearidonic acid. The another polyunsaturated fatty acid may be, for example, dihomo-γ-linolenic acid or eicosatetraenoic acid.

Additionally, the present invention encompasses a method of preventing or treating a condition caused by insufficient intake of polyunsaturated fatty acids comprising administering to the patient the composition above in an amount sufficient to effect prevention or treatment.

Moreover, the present invention also includes a further method for producing a polyunsaturated fatty acid. This method comprises the steps of: a) isolating a nucleic acid sequence comprising or complementary to a nucleotide sequence: i) encoding a polypeptide comprising an amino acid sequence having at least 90% identity to an amino acid sequence selected from the group consisting of SEQ ID NO:2, SEQ ID NO:4, SEQ ID NO:6 and SEQ ID NO:8 or ii) having at least 90% identity to a nucleotide sequence selected from the group consisting of SEQ ID NO:1, SEQ ID NO:3, SEQ ID NO:5 and SEQ ID NO:7; b) constructing a vector comprising: i) the isolated nucleotide sequence, ii) an isolated nucleotide sequence encoding an elongase and iii) an isolated nucleotide sequence encoding a Δ5-desaturase; c) introducing the vector into a host cell for a time and under conditions sufficient for expression of the Δ6-desaturase, the elongase and said Δ5-desaturase; and d) exposing the expressed Δ6-desaturase, the expressed elongase and the expressed Δ5-desaturase to a substrate polyunsaturated fatty acid in order to convert the substrate to a product polyunsaturated fatty acid, the product polyunsaturated fatty acid to another polyunsaturated fatty acid and the another polyunsaturated fatty acid to a final product polyunsaturated fatty acid. For example, the substrate polyunsaturated fatty acid may be linoleic acid, the product polyunsaturated fatty acid may be γ-linolenic acid, the another polyunsaturated fatty acid may be dihomo-γ-linolenic acid and the final product polyunsaturated fatty acid may be arachidonic acid. Alternatively, the substrate polyunsaturated fatty acid may be α-linolenic acid, the product polyunsaturated fatty acid may be stearidonic acid, the another polyunsaturated fatty acid may be eicosatetraenoic acid and the final product polyunsaturated fatty acid may be eicosapentaenoic acid.

Additionally, the present invention includes an isolated nucleic acid sequence or fragment thereof which hybridizes, under moderate or high stringency conditions, to a nucleic acid sequence selected from the group consisting of SEQ ID NO:1, SEQ ID NO:3, SEQ ID NO:5 and SEQ ID NO:7.

The present invention also encompasses an isolated nucleic acid or fragment thereof, which hybridizes, under moderate or high stringency conditions, to an isolated nucleic acid sequence encoding a polypeptide having desaturase activity, wherein the amino acid sequence of said polypeptide has at least 90% identity to an amino acid sequence selected from the group consisting of SEQ ID NO:2, SEQ ID NO:4, SEQ ID NO:6 and SEQ ID NO:8.

BRIEF DESCRIPTION OF THE DRAWINGS

FIG. 2 illustrates the GAP alignment of the translated amino acid sequence of (SEQ ID NO:2) and the *Mortierella alpina* Δ6-desaturase (SEQ ID NO:40).

FIG. 3 illustrates the comparison of the location of the various Met-encoding 'ATG' start codons (bold, underlined) created in the putative desaturase gene sequence (Del-D6) front *Delacroixia*, which encodes the related, presented amino acid sequence (Consensus=SEQ ID NO:41; pRDC8=SEQ ID NO:42; pRDC10=SEQ ID NO:43; pRDC12=SEQ ID NO:44).

FIGS. 4A and 4B illustrates the alignment of the putative amino acid sequence encoded by Del-D6 (in pRDC12)(see SEQ ID NO:8) (i.e., the Δ6-desaturase from *Delacroixia coronatus* ATCC 28565) and the *Mortierella alpina* Δ6-desaturase (see SEQ ID NO:40).

FIGS. 5A and 5B illustrates the alignment of the putative amino acid sequence encoded by Del-D6 (in PRDC12) (SEQ ID:3) with known Δ6-desaturase sequences from *Mortierella alpina* (Accession #AAF08685) (SEQ ID NO:40), *Phaeodactylwn tricornarum* (Accession #AAL92563) (SEQ ID NO:37), *Rhizopus oyzae* (Accession #AAS93682) (SEQ ID NO:38), *Pythium irregulare* (Accession # AAL13310) (SEQ ID NO: 39), and *Mucor circinelloides* (Accession #BAB69055) (SEQ ID NO:45). Identical residues are underlined and the conserved histidine-box motifs as well as the conserved cytochrome $b_5$ domain are boxed.

DETAILED DESCRIPTION OF THE INVENTION

Figure 1:
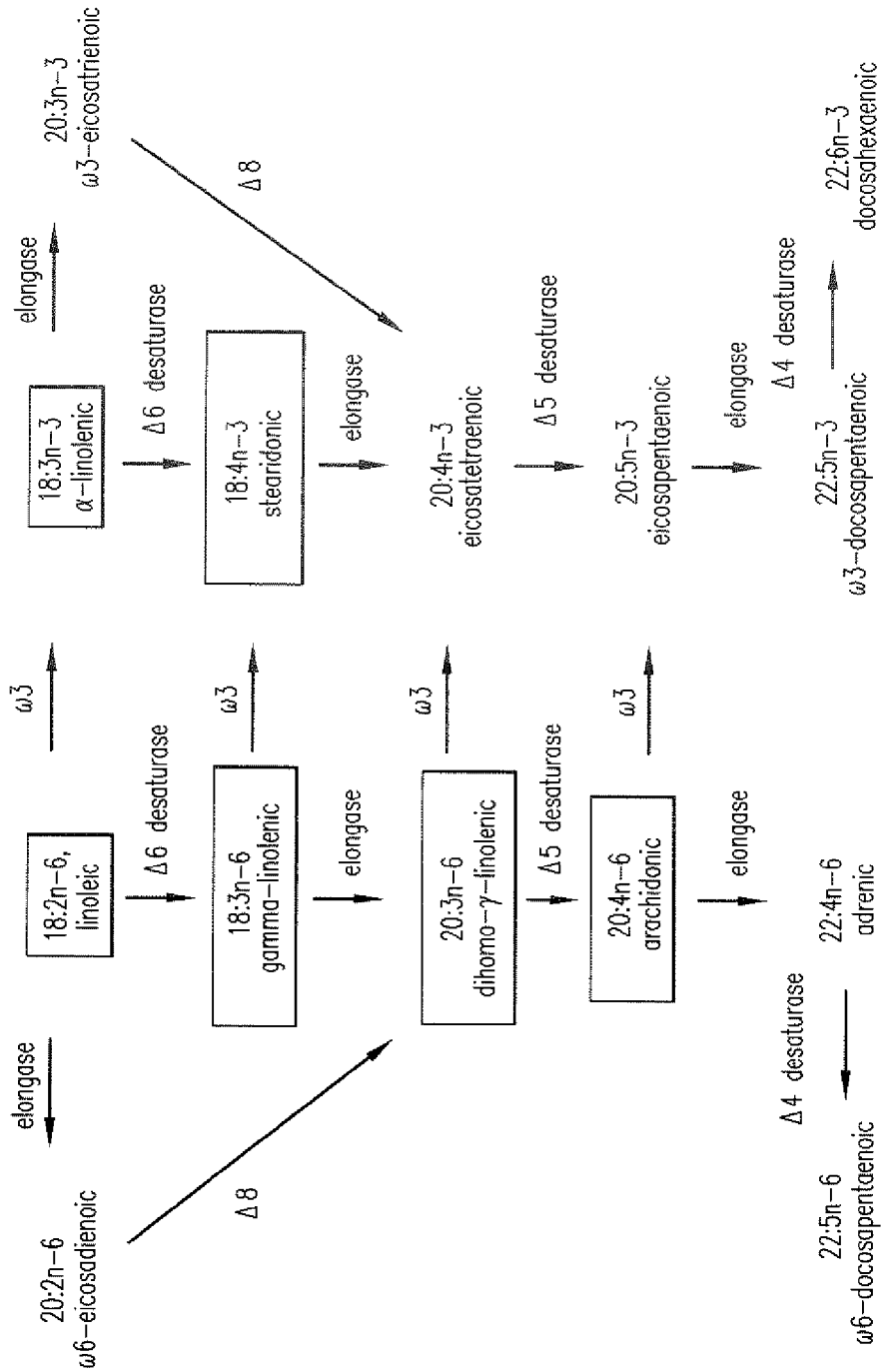
FIG. 1 illustrates the fatty acid biosynthetic pathway and the role of Δ6-desaturase in this pathway. Major pathway intermediates found in the total lipid profile of *Delacroixia* are boxed.

The subject invention relates to the nucleotide and translated amino acid sequences of the Δ6-desaturase genes derived from the fungus *Delacroixia coronata*. Furthermore, the subject invention also includes uses of the genes and of the enzymes encoded by this gene. For example, the genes and encoded, corresponding enzymes may be used in the production of polyunsaturated fatty acids such as, for instance, γ-linolenic acid and stearidonic acid which may be added to pharmaceutical compositions, nutritional compositions and to other valuable products.

The Δ6-Desaturase Genes and Enzymes Encoded Thereby

As noted above, the enzymes encoded by the Δ6-desaturase genes of the present invention are essential in the production of polyunsaturated fatty acids. SEQ ID NO:1 is the consensus nucleotide sequence of the putative Δ6-desaturase from *Delacraixia coronatus*, and SEQ ID NO:2 is the consensus amino acid sequence of the putative Δ6-desaturase from *Delacroixia coronatus*. The nucleotide sequences of the isolated *Delacroixia coronatus* Δ6-desaturase genes, which differed based upon the plasmid created (see Example II), are shown in SEQ ID NO: 3 (construct pRDC8), SEQ ID NO: 5 (construct pRDC10) and SEQ ID NO: 7 (construct pRDC12), and the amino acid sequences of the corresponding purified proteins are shown in SEQ ID NO: 4 (construct pRDC8) SEQ ID NO: 6 (construct pRDC10) and SEQ ID NO: 8 (construct pRDC12), respctively.

It should be noted that the present invention also encompasses isolated nucleotide sequences (and the corresponding encoded proteins) having sequences comprising, corresponding to, identical to, or complementary to at least about 70%, preferably at least about 80%, and more preferably at least about 90% identity to SEQ ID NO:1, SEQ ID NO:3, SEQ ID NO:5 or SEQ ID NO:7. (All integers (and portions thereof) between 70% and 100% are also considered to be within the scope of the present invention with respect to percent identity.) Such sequences may be derived from any source, either isolated from a natural source, or produced via a semi-synthetic route, or synthesized de novo. In particular, such sequences may be isolated or derived from sources other than described in the examples (e.g., bacteria, fungus, algae, *C. elegans*, mouse or human).

Furthermore, the present invention also encompasses fragments and derivatives of the nucleic acid sequences of the present invention (i.e., SEQ ID NO:1, SEQ ID NO:3, SEQ ID NO:5 and SEQ ID NO:7), as well as of the sequences derived from other sources, and having the above-described complementarity, identity or correspondence. Functional equivalents of the above full length sequences and fragments (i.e., sequences having Δ6-desaturase activity, as appropriate) are also encompassed by the present invention.

For purposes of the present invention, a "fragment" of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence.

The invention also includes a purified polypeptide which desaturates polyunsaturated fatty acids at the carbon 6 position and has at least about 70% amino acid similarity or identity, preferably at least about 80% amino acid similarity or identity and more preferably at least about 90% amino acid similarity or identity to the amino acid sequences of SEQ ID NO:2, SEQ ID NO:4, SEQ ID NO:6 or SEQ ID NO:8 of the above-noted proteins which are, in turn, encoded by the above-described nucleotide sequences.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g.; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity is defined as the degree of relatedness between two DNA segments. It is determined by measuring the ability of the sense strand of one DNA segment to hybridize with the anti-sense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes a PUFA having desaturase activity (i.e., Δ6-desaturase activity) and that is hybridizable, under moderately stringent conditions, to a nucleic acid having a nucleotide sequence comprising or complementary to the nucleotide sequences described above (see SEQ ID NO:1, SEQ ID NO:3, SEQ ID NO:5 and SEQ ID NO:7). A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold spring harbor Press, Cold Spring harbor, N.Y., 1989, as noted above and incorporated herein by reference. (See also Short Protocols in Molecular Biology, ed. Ausubel et al. and Tijssen, Techniques in Biochemistry and Molecular Biology-Hybridization with Nucleic Acid Probes, "Overview of principles of hybridization and the strategy of nucleic acid assays" (1993), both incorporated herein by reference.) Specifically, the choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1× Denhardt's solution and 0.5% SDS. Hybridization is carried out at about 68 degrees Celsius for about 3 to 4 hours for fragments of cloned DNA and for about 12 to about 16 hours for total eukaryotic DNA. For moderate stringencies, one may utilize filter pre-hybridizing and hybridizing with a solution of 3× sodium chloride, sodium citrate (SSC), 50% formamide (0.1 M of this buffer at pH 7.5) and 5× Denhardt's solution. One may then pre-hybridize at 37 degrees Celsius for 4 hours, followed by hybridization at 37 degrees Celsius with an amount of labeled probe equal to 3,000,000 cpm total for 16 hours, followed by a wash in 2×SSC and 0.1% SDS solution, a wash of 4 times for 1 minute each at room temperature and 4 times at 60 degrees Celsius for 30 minutes each. Subsequent to drying, one exposes to film. For lower stringencies, the temperature of hybridization is reduced to about 12 degrees Celsius below the melting temperature ($T_m$) of the duplex. The $T_m$ is known to be a function of the G-C content and duplex length as well as the ionic strength of the solution.

"Hybridization" requires that two nucleic acids contain complementary sequences. However, depending on the stringency of the hybridization, mismatches between bases may occur. As noted above, the appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". New promoters of various types useful in plant cells are constantly being discovered; numerous examples may be found in the compilation by Okamuro and Goldberg, *Biochemistry of Plants* 15:1-82 (1989). It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature (London)* 327:70-73; U.S. Pat. No. 4,945,050), or an *Agrobacterium*-mediated method using an appropriate Ti plasmid containing the transgene (Ishida Y. et al., 1996, *Nature Biotech.* 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Production of the Δ6-Desaturase Enyzme

Once the gene encoding the Δ6-desaturase enzyme has been isolated, it may then be introduced into either a prokaryotic or eukaryotic host cell through the use of a vector or construct. The vector, for example, a bacteriophage, cosmid or plasmid, may comprise the nucleotide sequence encoding the Δ6-desaturase enzyme, as well as any regulatory sequence (e.g., promoter) which is functional in the host cell and is able to elicit expression of the desaturase encoded by the nucleotide sequence. The regulatory sequence (e.g., promoter) is in operable association with, or operably linked to, the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell. For example, by including a Δ6-desaturase gene sequence of the present invention, an elongase gene sequence and a Δ5-desaturase gene sequence into the vector, one may co-express the encoded Δ6-desaturase, the encoded elongase, as well as the encoded Δ5-desaturase, respectively, in order to convert, for example, LA to ARA and ALA to EPA.

As noted above, once the vector has been constructed, it may then be introduced into the host cell of choice by methods known to those of ordinary skill in the art including, for example, transfection, transformation and electroporation (see *Molecular Cloning: A Laboratory Manual*, 2$^{nd}$ ed., Vol. 1-3, ed. Sambrook et al., Cold Spring Harbor Laboratory Press (1989)). The host cell is then cultured under suitable conditions permitting expression of the genes leading to the production of the desired PUFA, which is then recovered and purified.

Examples of suitable prokaryotic host cells include, for example, bacteria such as *Escherichia coli, Bacillus subtilis* as well as *Cyanobacteria* such as *Spirulina* spp. (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey, Candida* spp. such as *Yarrowia (Candida) lipolytica, Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., Δ6-desaturase), and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., *Science* 278: 2130-2133 (1997)). Gestation and birth are then permitted (see, e.g., U.S. Pat. Nos. 5,750,176 and 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463, 174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of a desaturase gene, or antisense desaturase transcripts, can alter the levels of specific PUFAs, or derivatives thereof, found in plant parts and/or plant tissues. The desaturase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean), cotton, safflower, sunflower, palm, coconut, maize, nuts, beans, peas or *Brassica napus* (canola)) or plant tissue may also be utilized as a host or host cell, respectively, for expression of the desaturase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the desaturase gene, as well as perhaps other desaturase genes and elongase genes, in order to provide seed oils that can be added to nutritional compositions, pharmaceutical compositions, animal feeds and cosmetics. Once again, a vector which comprises a DNA sequence encoding the desaturase operably linked to a promoter, will be introduced into the plant tissue or plant for a time and under conditions sufficient for expression of the desaturase gene. The vector may also comprise one or more genes that encode other enzymes, for example, $\Delta5$-desaturase, elongase, $\Delta12$-desaturase, $\Delta15$-desaturase, $\Delta17$-desaturase, and/or $\Delta19$-desaturase. The plant tissue or plant may produce the relevant substrate (e.g., linoleic acid or $\alpha$-linolenic acid) upon which the enzyme acts or a vector encoding enzymes which produce such substrates may be introduced into the plant tissue, plant cell or plant. In addition, substrate may be sprayed on plant tissues expressing the appropriate enzymes. Using these various techniques, one may produce PUFAs (e.g., n-6 unsaturated fatty acids such as $\omega6$-docosapentaenoic acid, or n-3 fatty acids such as docosahexaenoic acid) by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159, 135, 5,518,908); soybean (U.S. Pat. Nos. 5,569,834, 5,416, 011, McCabe et. al., *BiolTechnology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci. (USA)* 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603-618 (1990), Fromm et al., *BiolTechnology* 8:833 (1990), Koziel et al., *BiolTechnology* 11:194, (1993), Armstrong et al., *Crop Science* 35:550-557 (1995)); oat (Somers et al., *BiolTechnology* 10:1589 (1992)); orchard grass (Horn et al., *Plant Cell Rep.* 7:469 (1988)); rice (Toriyama et al., *Theor. Appl. Genet.* 205:34 (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., Bio/Technology 9:957 (1991)); rye (De la Pena et al., *Nature* 325:274 (1987)); sugarcane (Bower and Birch, *Plant J.* 2:409 (1992)); tall fescue (Wang et al., *Biol. Technology* 10:691 (1992)), and wheat (Vasil et al., *Biol. Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)).

The substrates which may be produced by the host cell either naturally or transgenically, as well as the enzymes which may be encoded by DNA sequences present in the vector, which is subsequently introduced into the host cell, are shown in FIG. 1.

Uses of the $\Delta6$-Desaturase Gene and Enzyme Encoded Thereby

As noted above, the isolated desaturase genes and the desaturase enzymes encoded thereby have many uses. For example, the gene and corresponding enzyme may be used indirectly or directly in the production of polyunsaturated fatty acids, for example, Δ6-desaturase may be used in the production of γ-linolenic acid or stearidonic acid. "Directly" is meant to encompass the situation where the enzyme directly converts the acid to another acid, the latter of which is utilized in a composition (e.g., the conversion of linoleic acid to γ-linolenic acid). "Indirectly" is meant to encompass the situation where an acid (e.g., α-linolenic acid) is converted to another acid (i.e., a pathway intermediate such as stearidonic acid) by the desaturase, and then the latter acid is converted to another acid by use of a desaturase or non-desaturase enzyme (e.g., stearidonic acid to eicosatetraenoic acid by an elongase). Also, the present invention includes "indirect" situations in which the PUFA is first converted to another polyunsaturated fatty acid by a non-Δ6-desaturase enzyme (for example, an elongase or another desaturase) and then converted to a final product via Δ6-desaturase. For example, linoleic acid may be converted to α-linolenic acid by a desaturase (i.e., Δ15-desaturase), and then converted to stearidonic acid by a Δ6-desaturase. These polyunsaturated fatty acids (i.e., those produced either directly or indirectly by activity of the Δ6-desaturase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced directly or indirectly by use of the desaturase gene, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, borage oil, fungal oil, black current oil, soy oil, and mono- and diglycerides. Examples of such carbohydrates include but are not limited to glucose, edible lactose and hydrolyzed starch. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements (e.g., adult nutritional products and oil), dietary substitutes, and rehydration compositions. Nutritional compositions of particular interest include but are not limited to those utilized for enteral and parenteral supplementation for infants, specialized infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substances boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196, 198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of desaturase expression, as well as the expression of other desaturases and elongases, can be used to modulate PUFA levels and ratios. The PUFAs produced in accordance with the present invention (e.g., AA and EPA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the desaturase genes, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr. Vol.* 57 (Suppl.) 732S-737S). Altered fatty acid metabolism and composition have been demonstrated in diabetic animals.

Furthermore, the compositions of the present invention, comprising PUFAs produced either directly or indirectly through the use of the desaturase enzymes, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol. Vol.* 83, p. 85-101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: lactase deficiency, lactose intolerance and galactosemia.

Features:
  Soy protein isolate to avoid symptoms of cow's-milk-protein allergy or sensitivity.
  Lactose-free formulation to avoid lactose-associated diarrhea.
  Low osmolality (240 mOs/kg water) to reduce risk of osmotic diarrhea.
  Dual carbohydrates (corn syrup and sucrose) designed to enhance carbohydrate absorption and reduce the risk of exceeding the absorptive capacity of the damaged gut.
  1.8 mg of Iron (as ferrous sulfate) per 100 Calories to help prevent iron deficiency.
  Recommended levels of vitamins and minerals.
  Vegetable oils to provide recommended levels of essential fatty acids.
  Milk-white color, milk-like consistency and pleasant aroma.
  Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula for Diarrhea:

Usage: As a short-term feeding for the dietary management of diarrhea in infants and toddlers.

Features:
  First infant formula to contain added dietary fiber from soy fiber specifically for diarrhea management.
  Clinically shown to reduce the duration of loose, watery stools during mild to severe diarrhea in infants.
  Nutritionally complete to meet the nutritional needs of the infant.
  Soy protein isolate with added L-methionine meets or exceeds an infant's requirement for all essential amino acids.
  Lactose-free formulation to avoid lactose-associated diarrhea.
  Low osmolality (240 mOsm/kg water) to reduce the risk of osmotic diarrhea.
  Dual carbohydrates (corn syrup and sucrose) designed to enhance carbohydrate absorption and reduce the risk of exceeding the absorptive capacity of the damaged gut.
  Meets or exceeds the vitamin and mineral levels recommended by the Committee on Nutrition of the American Academy of Pediatrics and required by the Infant Formula Act.
  1.8 mg of iron (as ferrous sulfate) per 100 Calories to help prevent iron deficiency.
  Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron:

Usage: As a beverage for infants, children and adults with an allergy or sensitivity to cow's-milk protein or an intolerance to sucrose. A feeding for patients with disorders for which lactose and sucrose should be avoided.

Features:
   Soy protein isolate to avoid symptoms of cow's-milk-protein allergy or sensitivity.
   Lactose-free formulation to avoid lactose-associated diarrhea (carbohydrate source is Polycose® Glucose Polymers).
   Sucrose free for the patient who cannot tolerate sucrose.
   Low osmolality (180 mOsm/kg water) to reduce risk of osmotic diarrhea.
   1.8 mg of iron (as ferrous sulfate) per 100 Calories to help prevent iron deficiency.
   Recommended levels of vitamins and minerals.
   Vegetable oils to provide recommended levels of essential fatty acids.
   Milk-white color, milk-like consistency and pleasant aroma.
   Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula with Iron Ready to Feed, 20 Cal/fl oz.:

Usage: When a soy feeding is desired.
   Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:

Usage: When an infant formula is needed: if the decision is made to discontinue breastfeeding before age 1 year, if a supplement to breastfeeding is needed or as a routine feeding if breastfeeding is not adopted.

Features:
   Protein of appropriate quality and quantity for good growth; heat-denatured, which reduces the risk of milk-associated enteric blood loss.
   Fat from a blend of vegetable oils (doubly homogenized), providing essential linoleic acid that is easily absorbed.
   Carbohydrate as lactose in proportion similar to that of human milk.
   Low renal solute load to minimize stress on developing organs.
   Powder, Concentrated Liquid and Ready To Feed forms.
   Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® NeoCare Premature Infant Formula with Iron:

Usage: For premature infants' special nutritional needs after hospital discharge. Similac NeoCare is a nutritionally complete formula developed to provide premature infants with extra calories, protein, vitamins and minerals needed to promote catch-up growth and support development.

Features:
   Reduces the need for caloric and vitamin supplementation. More calories (22 Cal/fl oz) than standard term formulas (20 Cal/fl oz).
   Highly absorbed fat blend, with medium-chain triglycerides (MCToil) to help meet the special digestive needs of premature infants.
   Higher levels of protein, vitamins and minerals per 100 calories to extend the nutritional support initiated in-hospital.
   More calcium and phosphorus for improved bone mineralization.
   Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready To Use, 24 Cal/fl oz.:

Usage: Designed to be mixed with human milk or to be fed alternatively with human milk to low-birth-weight infants.
   Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions:
    For patients on modified diets
    For elderly patients at nutrition risk
    For patients with involuntary weight loss
    For patients recovering from illness or surgery
    For patients who need a low-residue diet
    Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate. (See also ProSure®.)

B. ENSURE® BARS:

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:
    For patients who need extra calories, protein, vitamins and minerals.
    Especially useful for people who do not take in enough calories and nutrients.
    For people who have the ability to chew and swallow
    Not to be used by anyone with a peanut allergy or any type of allergy to nuts.
    Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed & soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN:

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:
    For patients who require additional calories, protein, vitamins, and minerals, such as patients recovering from general surgery or hip fractures, patients at risk for pressure ulcers, and patients on low-cholesterol diets.

Features:
    Low in saturated fat
    Contains 6 g of total fat and <5 mg of cholesterol per serving
    Rich, creamy taste Excellent source of protein, calcium, and other essential vitamins and minerals For low-cholesterol diets Lactose-free, easily digested Ingredients:

Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:

The protein source is a blend of two high-biologic-value proteins: casein and soy.

| | |
|---|---|
| Sodium and calcium caseinates | 85% |
| Soy protein isolate | 15% |

Fat:

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate:

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and other Nonchocolate Flavors:

| | |
|---|---|
| Sucrose | 60% |
| Maltodextrin | 40% |

Chocolate:

| | |
|---|---|
| Sucrose | 70% |
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:
For normal-weight or overweight patients who need extra nutrition in a supplement that contains 50% less fat and 20% fewer calories than ENSURE.
For healthy adults who do not eat right and need extra nutrition.

Features:
Low in fat and saturated fat
Contains 3 g of total fat per serving and <5 mg cholesterol
Rich, creamy taste
Excellent source of calcium and other essential vitamins and minerals
For low-cholesterol diets
Lactose-free, easily digested Ingredients:
French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:
The protein source is calcium caseinate.

| | |
|---|---|
| Calcium caseinate | 100% |

Fat:
The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:
ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other Nonchocolate Flavors:

| Sucrose | 51% |
|---|---|
| Maltodextrin | 49% |

Chocolate:

| Sucrose | 47.0% |
|---|---|
| Corn Syrup | 26.5% |
| Maltodextrin | 26.5% |

Vitamins and Minerals:
An 8-fl-oz serving of ENSURE LIGHT provides at least 25% of the RDIs for 24 key vitamins and minerals.

Caffeine:
Chocolate flavor contains 2.1 mg caffeine/8 fl oz.

E. ENSURE PLUS®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:
For patients who require extra calories and nutrients, but a normal concentration of protein, in a limited volume.
For patients who need to gain or maintain healthy weight.

Features:
Rich, creamy taste
Good source of essential vitamins and minerals

Ingredients:
Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein:
The protein source is a blend of two high-biologic-value proteins: casein and soy.

| Sodium and calcium caseinates | 84% |
|---|---|
| Soy protein isolate | 16% |

Fat:
The fat source is corn oil.

| Corn oil | 100% |
|---|---|

Carbohydrate:
ENSURE PLUS contains a combination of maltodextrin and sucrose. The mild sweetness and flavor variety (vanilla, chocolate, strawberry, coffee, buffer pecan, and eggnog), plus VAR1-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors:

| Corn Syrup | 39% |
|---|---|
| Maltodextrin | 38% |
| Sucrose | 23% |

Chocolate and Eggnog Flavors:

| Corn Syrup | 36% |
|---|---|
| Maltodextrin | 34% |
| Sucrose | 30% |

Vitamins and Minerals:
An 8-fl-oz serving of ENSURE PLUS provides at least 15% of the RDIs for 25 key Vitamins and minerals.

Caffeine:
Chocolate flavor contains 3.1 mg Caffeine/8 fl oz. Coffee flavor contains a trace amount of caffeine.

F. ENSURE PLUS® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:
For patients with increased calorie and protein needs, such as following surgery or injury.
For patients with limited volume tolerance and early satiety.

Features:
For supplemental or total nutrition
For oral or tube feeding
1.5 CaVmL,
High nitrogen
Calorically dense Ingredients:
Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. ENSURE® POWDER:

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions:
    For patients on modified diets
    For elderly patients at nutrition risk
    For patients recovering from illness/surgery
    For patients who need a low-residue diet Features:
    Convenient, easy to mix
    Low in saturated fat
    Contains 9 g of total fat and <5 mg of cholesterol per serving
    High in vitamins and minerals
    For low-cholesterol diets
    Lactose-free, easily digested
    Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein:
    The protein source is a blend of two high-biologic-value proteins: casein and soy.

| | |
|---|---|
| Sodium and calcium caseinates | 84% |
| Soy protein isolate | 16% |

Fat:
    The fat source is corn oil.

| | |
|---|---|
| Corn oil | 100% |

Carbohydrate:
    ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla:

| | |
|---|---|
| Corn Syrup | 35% |
| Maltodextrin | 35% |
| Sucrose | 30% |

H. ENSURE® PUDDING

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions:
    For patients on consistency-modified diets (e.g., soft, pureed, or full liquid)
    For patients with swallowing impairments Features:
    Rich and creamy, good taste
    Good source of essential vitamins and minerals
    Convenient-needs no refrigeration
    Gluten-free
    Nutrient Profile per 5 oz: Calories 250, Protein 10.9%, Total Fat 34.9%, Carbohydrate 54.2%

Ingredients:
    Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein:
    The protein source is nonfat milk.

| | |
|---|---|
| Nonfat milk | 100% |

Fat:
    The fat source is hydrogenated soybean oil.

| | |
|---|---|
| Hydrogenated soybean oil | 100% |

Carbohydrate:
    ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and other Nonchocolate Flavors:

| | |
|---|---|
| Sucrose | 56% |
| Lactose | 27% |
| Modified food starch | 17% |

Chocolate:

| | |
|---|---|
| Sucrose | 58% |
| Lactose | 26% |
| Modified food starch | 16% |

I. ENSURE® WITH FIBER:

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:
    For patients who can benefit from increased dietary fiber and nutrients Features:
    New advanced formula-low in saturated fat, higher in vitamins and minerals
    Contains 6 g of total fat and <5 mg of cholesterol per serving
    Rich, creamy taste
    Good source of fiber
    Excellent source of essential vitamins and minerals
    For low-cholesterol diets
    Lactose- and gluten-free Ingredients:
    Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein:
    The protein source is a blend of two high-biologic-value proteins-casein and soy.

| | |
|---|---|
| Sodium and calcium caseinates | 80% |
| Soy protein isolate | 20% |

Fat:
    The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of $\leq 30\%$ of total calories from fat, <10% of the calories from saturated fatty acids, and $\leq 10\%$ of total calories from polyunsaturated fatty acids.

Carbohydrate:
    ENSURE WITH FIBER contains a combination of maltodextrin and sucrose. The mild sweetness and flavor variety (vanilla, chocolate, and butter pecan), plus VARI-FLA-VORS® Flavor Pacs in pecan, cherry, strawberry, lemon, and orange, help to prevent flavor fatigue and aid in patient compliance.

Vanilla and other Nonchocolate Flavors:

| | |
|---|---|
| Maltodextrin | 66% |
| Sucrose | 25% |
| Oat Fiber | 7% |
| Soy Fiber | 2% |

Chocolate:

| | |
|---|---|
| Maltodextrin | 55% |
| Sucrose | 36% |
| Oat Fiber | 7% |
| Soy Fiber | 2% |

Fiber:
    The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:
    Caloric density is high at 1.5 Cal/mL (355 Cal/8 fl oz), to minimize the volume required to meet energy needs.
    The distribution of Calories in Oxepa is shown in Table A.

TABLE A

| Caloric Distribution of Oxepa | | | |
|---|---|---|---|
| | per 8 fl oz. | per liter | % of Cal |
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:
　Oxepa contains 22.2 g of fat per 8-fl oz serving (93.7 g/L).
　The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table B.
　Oxepa provides a balanced amount of polyunsaturated, monounsaturated, and saturated fatty acids, as shown in Table VI.
　Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE B

Typical Fatty Acid Profile

| Fatty Acids | % Total | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapentaenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE C

Fat Profile of Oxepa.

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz |
| | 40.1 mg/L |

Carbohydrate:
　The carbohydrate content is 25.0 g per 8-fl-oz serving (105.5 g/L).
　The carbohydrate sources are 45% maltodextrin (a complex carbohydrate) and 55% sucrose (a simple sugar), both of which are readily digested and absorbed.
　The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.
　Oxepa is lactose-free.
　Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:
　Oxepa contains 14.8 g of protein per 8-fl-oz serving (62.5 g/L).
　The total calorie/nitrogen ratio (150:1) meets the need of stressed patients.
　Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.
　The protein sources of Oxepa are 86.8% sodium caseinate and 13.2% calcium caseinate.
　The amino acid profile of the protein system in Oxepa meets or surpasses the standard for high quality protein set by the National Academy of Sciences.
　Oxepa is gluten-free.

The present invention may be illustrated by use of the following non-limiting examples:

EXAMPLE I

Design of Degenerate Oligonucleotides for the Isolation of Desaturases from *Delacroixia coronata* (ATCC 28565) and cDNA Synthesis The fatty acid composition analysis of the fungus *Delacroixia coronata* (*D. coronata*) (ATCC 28565) was investigated to determine the types and amounts of polyunsaturated fatty acids (PUFAs) it produced. This fungus was found to contain significant amounts (~19% of total lipid) of the PUFA arachidonic acid (ARA, C20:4n-6) (see FIG. 1). Thus, it was determined that *D. coronata* probably contains a Δ6-desaturase which converts linoleic acid (LA, C18:2n-6) to γ-linolenic acid (GLA, C18:3n-6) and a Δ5-desaturase which converts dihomo-γ-linolenic acid (DGLA, C20:3n-6) to ARA. The goal was therefore to isolate the predicted desaturase genes from *D. coronata* and to verify the functionality of the enzymes by expression in an alternate host.

The approach taken was to design degenerate oligonucleotides (primers) that represent amino acid motifs that are conserved in known front-end desaturases. These primers could be then used in a PCR reaction to identify a gene fragment containing the conserved regions present in the putative desaturase genes from *Delacroixia*. Since the only fungal desaturases identified, at the time, were the Δ5- and Δ6-desaturase genes from *Moruerella alpina* (Genbank accession numbers AF067650, AB020032, respectively), desaturase sequences from plants as well as animals were taken into consideration during the design of these degenerate primers. In particular, known Δ5- and Δ6-desaturase sequences from the following organisms were used for the design of these degenerate primers: *Mortierella alpina*, *Borago officinalis*, *Helianthus annuus*, *Brassica napus*, *Dicyyostelium discoideum*, *Rattus norvegicus*, *Mus musculus*, *Homo sapiens*, *Caenorhabdftis elegans*, *Arabidopsis thaliana*, and *Ricinus communis*. The degenerate primers used were as follows using the CODEHOP™ Blockmaker program:
   a. Protein motif 1 (SEQ ID NO:9): NH$_3$-VYD-VTEWVKRHPGG-CCCH Primer RO834 (SEQ ID NO:10): 5'-GTBTAYGAYGTBACCGARTGGGT-BAAGCGYCAYCCBGGHGGH-3'
   b. Protein Motif 2 (SEQ ID NO:11): NH$_3$-GASANW-WKHQHNVHH-COOH Primer RO835 (Forward) SEQ ID NO:12): 5-'GGHGCYTCCGCYAACTGGTG-GAAGCAYCAGCAYAACGTBCAYCAY-3, Primer RO836 (Reverse) (SEQ ID NO:13): 5-'RTGRTG-VACGTTRTGCTGRTGCTTCCACCAGT-TRGCGGARGCDCC-3'
   c. Protein Motif 3 (SEQ ID NO:14): NH$_3$-NYQIEHHLF-PTM-COOH Primer RO838 (Reverse)(SEQ ID NO:15): 5'-TTGATRGTCTARCTYGTRGTRGASAARG-GVTGGTAC-3'

All known desaturase amino acid sequences have a tripartite motif comprised of a group of eight conserved histidines: HX$_{(3-4)}$HX$_{(7-41)}$HX$_{(2-3)}$HHX$_{(61-189)}$HX$_{(2-3)}$HH (SEQ ID NO:16). The three histidine boxes are often used to identify putative desaturases. In addition, two more primers were designed based on the 2nd and 3rd conserved 'Histidine-box' found in known Δ6-desaturases.

These were:
  Primer RO753 (SEQ ID NO:17):
  5'-CATCATCATNGGRAANARRTGRTG-3'
  Primer RO754 (SEQ ID NO:18):
  5'-CTACTACTACTACAYCAYACNTAY ACNAAY-3'.

The degeneracy code for the oligonucleotide sequences was: B=C,G,T; H=A,C,T; S=C,G; R=A,G; V=A,C,G; Y=C,T; D=A,T,C; N=A,C,G,T To isolate genes encoding functional desaturase enzymes, the RNA was first prepared. *D. coronata* (ATCC 28565) cells were grown in BY+Media (#790, Difco, Detroit, Mich.) at room temperature for 4 days, in the presence of light, and with constant agitation (250 rpm) to obtain the maximum biomass. These cells were harvested by centrifugation at 5000 rpm for 10 minutes and rinsed in ice-cold RNase-free water. These cells were then lysed in a French press at 10,000 psi, and the lysed cells were directly collected into TE buffered phenol. Proteins from the cell lysate were removed by repeated phenol:chloroform (1:1 v/v) extraction, followed by a chloroform extraction. The nucleic acids from the aqueous phase were precipitated at −70° C. for 30 minutes using 0.3 M (final concentration) sodium acetate (pH 5.6) and one volume of isopropanol. The precipitated nucleic acids were collected by centrifugation at 15,000 rpm for 30 minutes at 4° C., vacuum-dried for 5 minutes and then treated with DNaseI (RNase-free) in 1× DNase buffer (20 mM Tris-Cl, pH 8.0; 5 mM MgCl$_2$) for 15 minutes at room temperature. The reaction was quenched with 5 mM EDTA (pH 8.0) and the RNA further purified using the Qiagen RNeasy Maxi kit (Qiagen, Valencia, Calif.), as per the manufacturer's protocol.

To prepare the cDNA, two PCR reactions were performed. The first PCR reaction was performed using the SuperScript Preamplification System for First Strand cDNA Synthesis Kit (Life Technologies, Rockville, Md.), with 0.5 μg of oligo dT primer and 5 μl RNA (1 μg/l), following the manufacturer's instructions. The second PCR reaction was performed using the degenerate primers RO834/RO838 (designed with the block maker program) and the first strand cDNA as target, in Perkin Elmer 9600. The PCR components were as follows: 2 μl of the first strand cDNA template, 1 μl 50× dNTP mix, 0.2 μM final concentration of each primer, 5 μl 10× KlenTaq PCR reaction buffer, and 1 μl of Advantage KlenTaq polymerase (Clonetech, Palo Alto, Calif.). Thermocycling was carried out as follows: an initial denaturation at 94° C. for 3 minutes, followed by 35 cycles of denaturation at 94° C. for 30 seconds; annealing at 60° C. for 30 seconds; and extension at 72° C. for 7 minute. This was followed by a final extension at 72° C. for 7 minutes. The reaction was separated on a 1% agarose gel, and approximately 1.3 Kb DNA fragment was excised and purified with the QiaQuick Gel Extraction Kit (Qiagen, Valencia, Calif.). The staggered ends on this fragment were 'filled-in' using T4 DNA polymerase (Life Technologies, Rockville, Md.) as per manufacturer's specifications, and this DNA fragment was cloned into the PCR-Blunt vector (Invitrogen, Carlsbad, Calif.). The recombinant plasmids were transformed into TOP10 supercompetent cells (Invitrogen, Carlsbad, Calif.) and 9 clones were partially sequenced. Three separate overlapping clones aligned to give a sequence of approximately 1080 bp.

The translated sequence corresponding to this fragment was used to search the GenBank database. This fragment was found to share highest sequence homology with the *Mortierella alpina* Δ6-desaturase (Genbank accession AF10510) (~53% sequence identity) (FIG. 2). Thus, the full-length gene encoding this putative desaturase was isolated to determine its activity when expressed in yeast.

EXAMPLE II

Preparation of RACE cDNA and Isolation of the Full Length Gene Sequence from *Delacroixia coronata* (ATCC 28565)

RACE (rapid amplification of cDNA ends) ready cDNA was used as a target for the reactions to isolate the full-length cDNA. To prepare RACE ready cDNA, approximately 5 μg of total RNA was used according to the manufacturer's direction with the GeneRacer™ kit (Invitrogen, Carlsbad, Calif.) and Superscript II™ enzyme (Invitrogen, Carlsbad, Calif.) for reverse transcription to produce cDNA target. For the initial amplification of the ends, the following thermocycling protocol was used in a Perkin Elmer 9600: initial melt at 94° C. for 2 minutes followed by 5 cycles of 94° C. for 30 seconds and 72° C. for 3 minutes, 10 cycles of 94° C. 30 seconds, 70° C. for 30 seconds, and 72° C. for 3 minutes and 20 cycles of 94° C. for 30 seconds, 68° C. for 30 seconds and 72° C. for 3 minutes, followed by an extension of 72° C. for 10 minutes.

The first PCR reactions were performed with 10 pMol of RO1526 (SEQ ID NO:19) (5'-TGC CTC CGT ATT CTC CCT TAA CCA CCA C-3') or RO1528 (SEQ ID NO:20) (5'-CTT CCA CAC TTT CCA CCC TGA TTC TTC CTG-3') and 30 pMol GeneRacer™ 3 prime primer (SEQ ID NO:21) (5'-GCT GTC AAC GAT ACG CTA CGT AAC G-3'); or RO1524 (SEQ ID NO:22) (5'TGA ATC CAA GTG GAG GGC ATG AAG ACA G-3') or RO1525 (SEQ ID NO:20) (SEQ ID NO:23) (5'-CGG AGG GGA TGA TAC CAA ACC AAC TAG AGC-3') and GeneRacer™ 5 prime primer (SEQ ID NO:24) (5'-CGA CTG GAG CAC GAG GAC ACT GA-3'). Each reaction contained 1 ul of cDNA in a final volume of 50 ul with Platinum Taq™ PCRx (Clonetech, Palo Alto, Calif.) using MgSO$_4$ according to the manufacturer's directions. A nested reaction was performed with 1 μl of the initial reaction, 10 pmol of nested primer RO1524 or RO1525 and 30 pmol of the GeneRacer™ nested 5 prime primer (SEQ ID NO:25) (5'-GGA CAC TGA CAT GGA CTG AAG GAG TA-3'); or nested primer RO1526 or RO1528 and GeneRacer™ nested 3 prime primer (SEQ ID NO:26) (5'-CGC TAC GTA ACG GCA TGA CAG TG 3') using the same conditions as the first reaction. Agarose gel analysis of the PCR products showed bands from approximately 400 bp to 1.3 Kb for the four reactions. Subsequent cloning into pCR Blunt (Invitrogen, Carlsbad, Calif.), transformation into Top10 competent cells (Invitrogen, Carlsbad, Calif.), and sequencing revealed an open reading frame of 466 amino acids. Based on the alignment with *M. alpina* Δ6desaturase, it was probable that this sequence contained the entire gene and that it was very likely a Δ6-desaturase. However, the translated amino acid sequence did not contain a start codon methionine (Met-ATG) at an appropriate site when aligned with the *M. alpina* Δ6-desaturase or some other fungal Δ6-desaturases.

Three alternative start codons were created at various sites on this putative desaturase gene (FIG. 3.) The full-length genes with these alternate start codons were designated pRDC8, pRDC10 and pRDC12 (FIG. 3). To create pRDC8, PCR was carried out using RACE cDNA using the following primers:(Stop-Ala, DraI)-Forward primer (SEQ ID NO:27): (5'-TTT AAA ATG AAT GGT AAT AAA ATT GCG GCG ATA AAA G-3'), and Reverse Primer (SEQ ID NO:28): (5'-TTT GCT AGC TTA AAT TTG GTC GTT GAT ATT GGT GGC-3').

PCR reactions were performed according to the manufacturer's directions using the Platinum Pfx Polymerase (Invitrogen, Carlsbad, Calif.). The full-length PCR product was digested with NheI and cloned into EcoRI-blunted (5') and NheI (3') sites of the pYX242 vector. This sequence utilized the 'Met' present upstream of the stop codon (SEQ ID NO:41) (MNGNKI*AIKEGAIL . . . ) as the start site, and the stop codon was convened to an 'Ala' resulting in the 5'seq (SEQ ID NO:42) (MNGNKIAAIKEGAIL . . . ) (FIG. 3).

To create pRDC 10, PCR was carried out using RACE cDNA using he following primers:(Ala-Met, Dra1) Forward primer (SEQ ID NO:29): (5'-TTT AAA ATG ATA AAA GAA GGG GCA ATA TTA ACC-3') and Reverse Primer (SEQ ID NO:30): (5'-CTA GCT AGC TTA AAT TTG GTC GTT GAT ATT GGT GGC-3').

The PCR reactions were performed according to the manufacturer's directions, using Platinum Pfx Polymerase (Invitrogen, Carlsbad, Calif.). The full-length PCR product was digested with NheI and cloned into EcoRI-blunted (5') and NheI (3') sites of the pYX242 vecton This converted the first Ala after the stop codon (SEQ ID NO:42) (*AIKEGAIL . . . ) to a Met (SEQ ID NO:43)(*MIKEGAIL . . . ), and this clone was designated as pRDC 10 (FIG. 3).

To isolate pRDC 12, genomic DNA (gDNA) was prepared using the DNeasy plant mini kit according to the manufacturer's directions (Qiagen, Valencia, Calif.). Primer RO1585 (SEQ ID NO:3)(5'-AAA GGA TCC AAT ATG TTA ATA GGC GGC GTT AAG-3') was designed to convert the third isoleucine after the stop codon (SEQ ID NO:43) (*AIKEG-AILTFML . . . ) to a methionine (SEQ ID NO:44) (*AIKEG-AILTFML . . . ) (FIG. 3). Primer RO 1584 (SEQ ID NO:32) (5'-ATC CTC GAG TTA AAT TTG GTC GTT GAT ATT GGT G-3') was designed for the 3' end of the full-length cDNA sequence. The PCR components were as follows: 3 μl of the gDNA, 1 μl 50× dNTP mix, 0.2 pM final concentration of primers RO1583 and RO1584 or RO1585 and RO1584, 2 μl MgSO4, 5 μl 10×PCR reaction buffer, and 0.2 μl of platinum TAQ HF polymerase (Clonetech, Palo Alto, Calif.). The following thermocycling protocol was used in a Perkin Elmer 9600: initial melt at 94° C. for 2 minutes followed by 5 cycles of 94° C. for 30 seconds and 72° C. for 3 minutes, 10 cycles of 94° C. 30 seconds, 70° C. for 30 seconds, and 72° C. for 3 minutes and 20 cycles of 94° C. for 30 seconds, 68° C. for 30 seconds and 72° C. for 3 minutes, followed by an extension of 72° C. for 10 minutes. The reaction was separated on a 1% agarose gel, and approximately 1.4 Kb DNA fragment was excised and purified with the QiaQuick Gel Extraction Kit (Qiagen, Valencia, Calif.). The full-length PCR product designated Del-D6, was digested with BamHI/XhoI and cloned into pESC-Ura vector. This construct was designated as pRDC-12. (Plasmid pRDC-12 was deposited with the American Type Culture Collection, 10801 University Boulevard, Manassas, Va. 20110 on May 18, 2004 and was accorded accession numbe PTA-5975). Alignment of the amino acid sequence of this putative desaturase (Del-D6) encoded by pRDC 12, with the Δ6-desaturase sequence from *Mortierella alpina*, revealed these proteins to share ~51% sequence identity with each other (FIGS. 4A and 4B).

Like other front-end desaturases, Del-D6 contains the three conserved 'histidine boxes' known to be required for the catalytic activity of these front end desaturase enzymes (Shanklin et at, *Biochemistry* 33 (43):12787-94 (1994), Sayanova et at, *Plant Physiol*. 121(2):641-46 (1999), and Periera et al., *Prostaglandins Leukot. Essent. Fatty Acids* 68(2):97-106 (2003))(FIGS. 5A and 5B). Histidine Box 1 (SEQ ID NO:33): HDFLH Histidine Box 2 (SEQ ID NO:34): HNTHH Histidine Box 3 (SEQ ID NO:35): QVEHH In addition, this sequence also contained a cytoebrome b5 domain at the 5'-end (HPGG motif (SEQ ID NO:36)(FIGS. 5A and 5B) implying that it uses cytochrome b5 as an electron donor during the desaruration reaction, as seen with other fungal and algal Δ6-desaturases (Periera et al., *Prostaglandins Leukot. Essent. Fatty Acids* 68(2):97-106 (2003)). The overall G+C content of this gene is 41.9%.

EXAMPLE III

Expression of Plasmids Containing Putative Desaturases in Yeast

All three plasmids were transformed into competent *Saccharomyces cerevisiae* strain 334. Yeast transformation was carried out using the Alkali-Cation Yeast Transformation Kit (BIO 101, Vista, Calif.) according to conditions specified by the manufacturer. Transformants were selected for uracil auxotrophy on media lacking uracil (DOB [-Ura]). To detect the specific desaturase activity of these clones, transformants were grown in the presence of 50 μM specific fatty acid substrates as listed below:

a. Linoleic acid (LA, C18:2n-6) (conversion to α-linolenic acid would indicate Δ15-desaturase activity and conversion to γ-linolenic acid would indicate Δ6-desaturase activity);

b. Alpha-linolenic acid (ALA, C18:3n-3) (conversion to stearidonic acid would indicate Δ6-desaturase activity);

c. (C20:2n-6) (conversion to dihomo-gammα-linolenic acid would indicate Δ8-desaturase activity);

d. (C20:3n-3) (conversion to eicosatetraenoic acid would indicate Δ8-desaturase activity);

e. Dihomo-γ-linolenic acid (DGLA, C20:3n-6) (conversion to arachidonic acid would indicate Δ8-desaturase activity);

f. Eicosatetraenoic acid (ETA, C20:4n-3) (conversion to eicosapentaenoic acid would indicate Δ5-activity);

g. Adrenic acid (ADA, C22:4n-6) (conversion to ω6-docosapentaenoic acid would indicate Δ4-desaturase activity); and h. ω3-docosapentaenoic acid (DPA, C22:4n-6) (conversion to docosahexaenoic acid would indicate Δ4-desaturase activity).

The negative control strain was *S. cerevisiae* 334 containing the unaltered pYX242 vector, and these were grown simultaneously.

The cultures were vigorously agitated (250 rpm) and grown for 48 hours a 24° C. in the presence of 50 μM (final concentration) of the various substrates in 50 ml of media lacking uracil after inoculation with overnight growth of single colonies in yeast peptone dextrose broth (YPD) at 30° C. The cells were pelleted, and the pellets vortexed in methanol; chloroform was added along with tridecanoin (as an internal standard). These mixtures were incubated for at least an hour at room temperature or at 4° C. overnight. The chloroform layer was extracted and filtered through a Whatman filter with 1 gm anhydrous sodium sulfate to remove particulates and residual water. The organic solvents were evaporated at 40° C. under a stream of nitrogen. The extracted lipids were then derivitized to fatty acid methyl esters (FAME) for gas chromatography analysis (GC) by adding 2 ml of 0.5 N potassium hydroxide in methanol to a closed tube. The samples were heated to 95° C.-100° C. for 30 minutes and cooled to room temperature. Approximately 2 ml of 14% borontrifluoride in methanol was added and the heating repeated. After the extracted lipid mixture cooled, 2 ml of water and 1 ml of hexane were added to extract the fatty acid methyl esters (FAME) for analysis by GC. The percent conversion was calculated by dividing the product produced by the sum of (the product produced+the substrate added) and then multiplying by 100.

The results showed conversion of LA to GLA and ALA to STA. This would indicate Δ6-desaturase activity (see Table 1).

TABLE 1

Percent Conversion of Different Substrate Concentrations to Product

| | pYX242 Control | PRDC8 | pRDC10 | pRDC12 |
|---|---|---|---|---|
| C18:2n-6 → C18:3n-6 | 0 | 4.1 | 4.6 | 35.1 |
| C20:2n-6 → C20:3n-6 | 0 | 0 | 0 | 0 |
| C20:3n-6 → C20:4n-6 | 0 | 0 | 0 | 0 |
| C22:4n-6 → C22:5n-6 | 0 | 0 | 0 | 0 |
| C18:3n-3 → C18:4n-3 | 0.7 | 5 | 6 | 34.5 |
| C20:3n-3 → C20:4n-3 | 0 | 0 | 0 | 0 |
| C20:4n-3 → C20:5n-3 | 0 | 0 | 0 | 0 |
| C22:5n-3 → C22:6n-3 | 0 | 0 | 0 | 0 |

C18:2n-6 to C18:3n-6 (Linolenic acid to α-linolenic acid)
C18:3n-3 to C18:4n-3 (α-linolenic acid to stearidonic acid)

C18:2n-6 to C18:3n-6 (Linoleic acid to α-linolenic acid)
C18:3n-3 to C18:4n-3 (α-linolenic acid to stearidonic acid)

This data shows unequivocally that this gene indeed encodes a Δ6-desaturase, with no Δ5-, Δ8- or Δ4-desaturase activity.

EXAMPLE IV

Co-Expression of Del-D6 (Δ6-Desaturase from *Delacroixia*) with the *Mortierella alpina* Elongase in Yeast The plasmid pRDC-12 was co-transformed with pRSP-46, a clone that contains a *M. alpina* elongase gene from pRPBG-2 (see U.S. published patent application no. US 2003/0177508A1 incorporated herein in its entirety by reference). Table 2 shows that when 50 μM of the substrate LA (C18:2n-6) was added, the desaturase converted the LA to GLA, and the elongase was able to add two carbons to GLA to produce DGLA. No DGLA was produced by the control transformation 334(pYX242/pESC-Ura). Also, when 50 μM of the substrate ALA (18:3n-3) was added, the desaturase converted the ALA to STA, and the elongase was able to add two carbons to STA to produce ETA. No ETA was produced by the control transformation 334(pYX242/pESC-Ura). Thus, *D. coronata* Δ6-desaturase was able to produce a product in a heterologous expression system that was the substrate of another heterologous enzyme (the *M. alpina* elongase) from the PUFA biosynthetic pathway to produce the expected PUFA. This demonstrates that Δ6-desaturase can indeed work with other heterologous enzymes in the PUFA pathway in a heterologous expression system such as yeast.

TABLE 2

Percent Conversion of Different Substrate Concentrations to Product

| | Substrate incorporated | Desaturated product | Elongated product |
|---|---|---|---|
| PYX242/ pESC-Ura (control) + LA | 62.45 | 0 | 0 |
| pRDC-12/ pRSP-46 (elongase) + LA | 59.2 | 24.15 | 6.88 |
| pYX242/ pESC-Ura (control) + ALA | 37.25 | 0 | 0 |
| pRDC-12/ pRSP-46 (elongase) + ALA | 67.82 | 19.75 | 5.84 |

EXAMPLE V

Identification of Δ6-Desaturase Homologues from other PUFA-Producing Organisms

Δ6-desaturases are predicted to exist in a number of PUFA-producing fungi and algae based on the presence of GLA (18:3n-6), ARA (20:4n-6) and/or EPA (20:5n-3) in these organisms upon analysis of their total fatty acid profiles. Using the degenerate primers set RO834 (SEQ ID NO:8) and RO838 (SEQ ID NO:13) in a PCR reaction similar to that described in Example I, it is possible to isolate fragments corresponding to the Δ6-desaturase genes from these organisms, followed by the full-length gene isolation using the protocol described in Example I. Organisms that can be used to isolate Δ6-desaturase genes would belong to the genera: Fungi such as *Cunninghamella, Rhizopus, Gongronella, Allamyces, Synchytrium, Achlya, Phycomyces, Choanephora, Helicostylum, Entomopthora*; Microalgae such as *Chlorella, Dunaliella, Lauderia, Fucus, Sargassum, Layengaria, Colpomenia, Plocamium, Rhodomella, Gelidium, Polysiphonia, Chondrus* (Folia Microbiol. (1992) 37: 357-359, Stredanska S. & Sajbidor J.; Appl. Microbiol. Biotechnol. (1991) 35: 421-430, Radwan S. S.; Biochum. Biophys. ACTA (1965) 98: 230-237, Shaw R.).

What is claimed is:

1. An isolated nucleic acid sequence comprising or complementary to a nucleotide sequence encoding a polypeptide having Δ6-desaturase activity, wherein the amino acid sequence of said polypeptide has at least 95% identity to SEQ ID NO:8.

2. An isolated nucleic acid sequence comprising or complementary to a nucleotide sequence having at least 95% identity to SEQ ID NO:7, wherein said nucleotide sequence encodes a polypeptide having Δ6-desaturase activity.

3. The isolated nucleic acid sequence of claim 1 or claim 2 wherein said sequence encodes a functionally active desaturase which utilizes a polyunsaturated fatty acid as a substrate.

4. The nucleotide sequence of claim 1 or 2 wherein said sequence is isolated from a fungus.

5. The nucleotide sequence of claim 4 wherein said fungus is *Delacroixia coronata*.

6. A purified polypeptide encoded by said nucleotide sequence of claims 1 or 2.

7. A purified polypeptide which desaturates polyunsaturated fatty acids at carbon 6 and comprises an amino acid sequence having at least 95% identity to SEQ ID NO:8.

8. A method of producing a desaturase comprising the steps of:

a) isolating a nucleic acid sequence comprising or complementary to a nucleotide sequence:

i) encoding a polypeptide comprising an amino acid sequence having at least 95% identity to SEQ ID NO:8 or ii) having at least 95% identity to SEQ ID NO:7;

b) constructing a vector comprising: i) said isolated nucleotide sequence operably linked to ii) a regulatory sequence;

c) introducing said vector into a host cell for a time and under conditions sufficient for expression of said desaturase.

9. A vector comprising:

a) an isolated nucleic acid sequence comprising or complementary to a nucleotide sequence:

i) encoding a polypeptide comprising an amino acid sequence having at least 95% identity to SEQ ID NO:8 and Δ6-desaturase activity or ii) having at least 95% identity to SEQ ID NO:7 and encoding a polypeptide having Δ6-deasturase activity, operably linked to b) a regulatory sequence.

10. An isolated host cell comprising said vector of claim 9.

11. The isolated host cell of claim 10, wherein the host cell is a plant cell.

* * * * *

SEQUENCE LISTING

<160> NUMBER OF SEQ ID NOS: 45

<210> SEQ ID NO 1
<211> LENGTH: 1079
<212> TYPE: DNA
<213> ORGANISM: Delacroixia coronatus

<400> SEQUENCE: 1

```
gtttatgacg tgaccgagtg ggtcaagcgt caccccggcg gtcccattat tttaacccat     60
gttggtagag atggtactga tgctttccac actttccacc ctgattcttc ctgggaaacc    120
cttgccaatt actatgttgg agatattcac cccgatgatg ttattaatca agattctaag    180
ccttcctttt taaccgatat aagaaagctt aaggataagt actataagct cggatacttc    240
aatgccgata tgggtttcta tacttacaag tgtttatcta ctgtatccat tttgccctc     300 tctgttacta tcttatataa cttcagctct agttggtttg gtatcatccc ctccgctatg    360
atcatgggct tattttggca acaatgtggc tggttatctc acgatttcct ccatcatcaa    420
gttagcgaca atagagatat caataacgcc attggtggtc tcttctatgg tgccgtttgt    480
caaggtttct ctatgtcttg gtggaaagat aagcacaata cccatcacgc tgcccctaac    540
gtttataacg aagaccccga tatcgatacc cacccctttt tagcctggtc cgaacaagct    600
atggaacttt atgccgactt aaatgaccaa gaaatgtctt ctagaatgaa gaagttcatg    660
ctcactaacc aagctatcat ctacttcccc ttattgactt ttgctagatt atcatggtgt    720
acctacagtt tatggttctg cttctctaga ggaactctta gcaaccccaa caagatcccc    780
attaatattg aattcagcga aaaggccgct ttactcaccc attggttcat taccttatcc    840
atcactgtct tcatgccctc cacttggatt caatcccttg tattctttat tgtttgtcaa    900
gcctcttgtg gtgtcctcct tgcctccgta ttctccctta accacaacgg tatggccgta    960
atctccactg aagaagccga taacatggac ttctacacca agcaagttat tactggtcgt   1020
gatgttaccc cctctcactt cattcaatgg ttctgtggag gcttaaacta tcagattga    1079
```

<210> SEQ ID NO 2
<211> LENGTH: 359
<212> TYPE: PRT
<213> ORGANISM: Delacroixia coronatus

<400> SEQUENCE: 2

```
Val Tyr Asp Val Thr Glu Trp Val Lys Arg His Pro Gly Gly Pro Ile
 1               5                  10                  15

Ile Leu Thr His Val Gly Arg Asp Gly Thr Asp Ala Phe His Thr Phe
            20                  25                  30

His Pro Asp Ser Ser Trp Glu Thr Leu Ala Asn Tyr Tyr Val Gly Asp
        35                  40                  45

Ile His Pro Asp Asp Val Ile Asn Gln Asp Ser Lys Pro Ser Phe Leu
    50                  55                  60

Thr Asp Ile Arg Lys Leu Lys Asp Lys Tyr Tyr Lys Leu Gly Tyr Phe
65                  70                  75                  80

Asn Ala Asp Met Gly Phe Tyr Thr Tyr Lys Cys Leu Ser Thr Val Ser
                85                  90                  95

Ile Phe Ala Leu Ser Val Thr Ile Leu Tyr Asn Phe Ser Ser Ser Trp
            100                 105                 110

Phe Gly Ile Ile Pro Ser Ala Met Ile Met Gly Leu Phe Trp Gln Gln
        115                 120                 125
```

```
Cys Gly Trp Leu Ser His Asp Phe Leu His His Gln Val Ser Asp Asn
            130                 135                 140

Arg Asp Ile Asn Asn Ala Ile Gly Gly Leu Phe Tyr Gly Ala Val Cys
145                 150                 155                 160

Gln Gly Phe Ser Met Ser Trp Trp Lys Asp Lys His Asn Thr His His
                165                 170                 175

Ala Ala Pro Asn Val Tyr Asn Glu Asp Pro Asp Ile Asp Thr His Pro
            180                 185                 190

Phe Leu Ala Trp Ser Glu Gln Ala Met Glu Leu Tyr Ala Asp Leu Asn
        195                 200                 205

Asp Gln Glu Met Ser Ser Arg Met Lys Lys Phe Met Leu Thr Asn Gln
    210                 215                 220

Ala Ile Ile Tyr Phe Pro Leu Leu Thr Phe Ala Arg Leu Ser Trp Cys
225                 230                 235                 240

Thr Tyr Ser Leu Trp Phe Cys Phe Ser Arg Gly Thr Leu Ser Asn Pro
                245                 250                 255

Asn Lys Ile Pro Ile Asn Ile Glu Phe Ser Glu Lys Ala Ala Leu Leu
            260                 265                 270

Thr His Trp Phe Ile Thr Leu Ser Ile Thr Val Phe Met Pro Ser Thr
        275                 280                 285

Trp Ile Gln Ser Leu Val Phe Phe Ile Val Cys Gln Ala Ser Cys Gly
    290                 295                 300

Val Leu Leu Ala Ser Val Phe Ser Leu Asn His Asn Gly Met Ala Val
305                 310                 315                 320

Ile Ser Thr Glu Glu Ala Asp Asn Met Asp Phe Tyr Thr Lys Gln Val
                325                 330                 335

Ile Thr Gly Arg Asp Val Thr Pro Ser His Phe Ile Gln Trp Phe Cys
            340                 345                 350

Gly Gly Leu Asn Tyr Gln Ile
        355

<210> SEQ ID NO 3
<211> LENGTH: 1422
<212> TYPE: DNA
<213> ORGANISM: Delacroxia coronatus

<400> SEQUENCE: 3
atgaatggta ataaaattgc ggcgataaaa gaaggggcaa tattaacctt tattttaata      60
ggcggcgtta agttattcag aagaagcgaa ctcaatactc acacctcttc aaaagatatt     120
ctaaccagca aggtatacgc tcccgcttat accatcatcg ataacaaagt ctacgatgtt     180
cgcgacttca ttttagacca ccctggaggt cccattattt aacccatgt tggtagagat     240 ggtactgatg ctttccacac tttccaccct gattcttcct gggaaaccct tgccaattac     300
tatgttggag atattcaccc cgatgatgtt attaatcaag attctaagcc ttccttttta     360
accgatataa gaaagcttaa ggataagtac tataagctcg atacttcaa tgccgatatg      420 ggtttctata cttacaagtg tttatctact gtatccattt ttgccctctc tgttactatc     480
ttatataact tcagctctag ttggtttggt atcatcccct ccgctatgat catgggctta     540
ttttggcaac aatgtggctg gttatctcac gattcctcc atcatcaagt tagcgacaat     600
agagatatca taacgccat tggtggtctc ttctatggtg ccgtttgtca aggtttctct      660
atgtcttggt ggaagataa gcacaatacc catcacgctg cccctaacgt ttataacgaa     720
gaccccgata tcgatacccca ccctttttta gcctggtccg aacaagctat ggaactttat     780
```

```
gccgacttaa atgaccaaga atgtcttct  agaatgaaga agttcatgct cactaaccaa      840
gctatcatct acttcccctt attgactttt gctagattat catggtgtac ctacagttta      900
tggttctgct tctctagagg aactcttagc aaccccaaca agatcccat  taatattgaa      960 ttcagcgaaa aggccgcttt actcacccat tggttcatta ccttatccat cactgtcttc     1020
atgccctcca cttggattca atcccttgta ttctttattg tttgtcaagc ctcttgtggt     1080
gtcctccttg cctccgtatt ctcccttaac cacaacggta tggccgtaat ctccactgaa     1140
gaagccgata acatggactt ctacaccaag caagttatta ctggtcgtga tgttaccccc     1200
tctcacttca ttcaatggtt ctgtggaggc ttaaactacc aagtagagca tcacttattc     1260
cccgcccttc ctagacactc tctccctaaa gttcaagccg atattgaagc cctctgcaaa     1320
aagcacggta ttccttacca tatgacaggc ttcattgatg gaactaagga ggtattagat     1380
agattacaaa aaattgccac caatatcaac gaccaaattt aa                        1422
```

<210> SEQ ID NO 4
<211> LENGTH: 473
<212> TYPE: PRT
<213> ORGANISM: Delacroxia coronatus

<400> SEQUENCE: 4

```
Met Asn Gly Asn Lys Ile Ala Ala Ile Lys Glu Gly Ala Ile Leu Thr
  1               5                  10                  15

Phe Ile Leu Ile Gly Gly Val Lys Leu Phe Arg Arg Ser Glu Leu Asn
             20                  25                  30

Thr His Thr Ser Ser Lys Asp Ile Leu Thr Ser Lys Val Tyr Ala Pro
         35                  40                  45

Ala Tyr Thr Ile Ile Asp Asn Lys Val Tyr Asp Val Arg Asp Phe Ile
     50                  55                  60

Leu Asp His Pro Gly Gly Pro Ile Ile Leu Thr His Val Gly Arg Asp
 65                  70                  75                  80

Gly Thr Asp Ala Phe His Thr Phe His Pro Asp Ser Ser Trp Glu Thr
                 85                  90                  95

Leu Ala Asn Tyr Tyr Val Gly Asp Ile His Pro Asp Val Ile Asn
            100                 105                 110

Gln Asp Ser Lys Pro Ser Phe Leu Thr Asp Ile Arg Lys Leu Lys Asp
        115                 120                 125

Lys Tyr Tyr Lys Leu Gly Tyr Phe Asn Ala Asp Met Gly Phe Tyr Thr
    130                 135                 140

Tyr Lys Cys Leu Ser Thr Val Ser Ile Phe Ala Leu Ser Val Thr Ile
145                 150                 155                 160

Leu Tyr Asn Phe Ser Ser Ser Trp Phe Gly Ile Ile Pro Ser Ala Met
                165                 170                 175

Ile Met Gly Leu Phe Trp Gln Gln Cys Gly Trp Leu Ser His Asp Phe
            180                 185                 190

Leu His His Gln Val Ser Asp Asn Arg Asp Ile Asn Asn Ala Ile Gly
        195                 200                 205

Gly Leu Phe Tyr Gly Ala Val Cys Gln Gly Phe Ser Met Ser Trp Trp
    210                 215                 220

Lys Asp Lys His Asn Thr His Ala Ala Pro Asn Val Tyr Asn Glu
225                 230                 235                 240

Asp Pro Asp Ile Asp Thr His Pro Phe Leu Ala Trp Ser Glu Gln Ala
                245                 250                 255
```

```
Met Glu Leu Tyr Ala Asp Leu Asn Asp Gln Glu Met Ser Ser Arg Met
            260                 265                 270

Lys Lys Phe Met Leu Thr Asn Gln Ala Ile Ile Tyr Phe Pro Leu Leu
        275                 280                 285

Thr Phe Ala Arg Leu Ser Trp Cys Thr Tyr Ser Leu Trp Phe Cys Phe
        290                 295                 300

Ser Arg Gly Thr Leu Ser Asn Pro Asn Lys Ile Pro Ile Asn Ile Glu
305                 310                 315                 320

Phe Ser Glu Lys Ala Ala Leu Leu Thr His Trp Phe Ile Thr Leu Ser
                325                 330                 335

Ile Thr Val Phe Met Pro Ser Thr Trp Ile Gln Ser Leu Val Phe Phe
            340                 345                 350

Ile Val Cys Gln Ala Ser Cys Gly Val Leu Leu Ala Ser Val Phe Ser
        355                 360                 365

Leu Asn His Asn Gly Met Ala Val Ile Ser Thr Glu Glu Ala Asp Asn
    370                 375                 380

Met Asp Phe Tyr Thr Lys Gln Val Ile Thr Gly Arg Asp Val Thr Pro
385                 390                 395                 400

Ser His Phe Ile Gln Trp Phe Cys Gly Gly Leu Asn Tyr Gln Val Glu
                405                 410                 415

His His Leu Phe Pro Ala Leu Pro Arg His Ser Leu Pro Lys Val Gln
            420                 425                 430

Ala Asp Ile Glu Ala Leu Cys Lys Lys His Gly Ile Pro Tyr His Met
        435                 440                 445

Thr Gly Phe Ile Asp Gly Thr Lys Glu Val Leu Asp Arg Leu Gln Lys
    450                 455                 460

Ile Ala Thr Asn Ile Asn Asp Gln Ile
465                 470

<210> SEQ ID NO 5
<211> LENGTH: 1401
<212> TYPE: DNA
<213> ORGANISM: Delacroixia coronatus

<400> SEQUENCE: 5
atgataaaag aagggcaat attaaccttt attttaatag gcggcgttaa gttattcaga      60
agaagcgaac tcaatactca cacctcttca aaagatattc taaccagcaa ggtatacgct     120
cccgcttata ccatcatcga taacaaagtc tacgatgttc gcgacttcat tttagaccac     180
cctggaggtc ccattatttt aacccatgtt ggtagagatg gtactgatgc cttccacact     240
ttccaccctg attcttcctg ggaaacccct gccaattact atgttggaga tattcacccc     300
gatgatgtta ttaatcaaga ttctaagcct tcctttttaa ccgatataag aaagcttaag     360
gataagtact ataagctcgg atacttcaat gccgatatgg gtttctatac ttacaagtgt     420
ttatctactg tatccatttt tgccctctct gttactatct tatataactt cagctctagt     480
tggtttggta tcatcccctc cgctatgatc atgggcttat tttggcaaca atgtggctgg     540
ttatctcacg atttcctcca tcatcaagtt agcgacaata gagatatcaa taacgccatt     600
ggtggtctct ctatggtgc cgtttgtcaa ggtttctcta tgtcttggtg aaagataag      660
cacaataccc atcacgctgc ccctaacgtt ataacgaag ccccgatat cgataccac       720
ccctttttag cctggtccga acaagctatg gaactttatg ccgactaaaa tgaccaagaa     780
atgtcttcta gaatgaagaa gttcatgctc actaaccaag ctatcatcta cttccccta     840
ttgacttttg ctagattatc atggtgtacc tacagtttat ggttctgctt ctctagagga     900
```

-continued

```
actcttagca accccaacaa gatccccatt aatattgaat tcagcgaaaa ggccgcttta      960
ctcacccatt ggttcattac cttatccatc actgtcttca tgccctccac ttggattcaa     1020
tcccttgtat tctttattgt ttgtcaagcc tcttgtggtg tcctccttgc ctccgtattc     1080
tcccttaacc acaacggtat ggccgtaatc tccactgaag aagccgataa catggacttc     1140
tacaccaagc aagttattac tggtcgtgat gttaccccct ctcacttcat tcaatggttc     1200
tgtggaggct aaaactacca agtagagcat cacttattcc ccgcccttcc tagacactct     1260
ctccctaaag ttcaagccga tattgaagcc ctctgcaaaa agcacggtat tccttaccat     1320
atgacaggct tcattgatgg aactaaggag gtattagata gattacaaaa aattgccacc     1380
aatatcaacg accaaattta a                                               1401
```

<210> SEQ ID NO 6
<211> LENGTH: 466
<212> TYPE: PRT
<213> ORGANISM: Delacroixia coronatus

<400> SEQUENCE: 6

```
Met Ile Lys Glu Gly Ala Ile Leu Thr Phe Ile Leu Ile Gly Gly Val
 1               5                  10                  15

Lys Leu Phe Arg Arg Ser Glu Leu Asn Thr His Thr Ser Ser Lys Asp
             20                  25                  30

Ile Leu Thr Ser Lys Val Tyr Ala Pro Ala Tyr Thr Ile Ile Asp Asn
         35                  40                  45

Lys Val Tyr Asp Val Arg Asp Phe Ile Leu Asp His Pro Gly Gly Pro
     50                  55                  60

Ile Ile Leu Thr His Val Gly Arg Asp Gly Thr Asp Ala Phe His Thr
 65                  70                  75                  80

Phe His Pro Asp Ser Ser Trp Glu Thr Leu Ala Asn Tyr Tyr Val Gly
                 85                  90                  95

Asp Ile His Pro Asp Asp Val Ile Asn Gln Asp Ser Lys Pro Ser Phe
            100                 105                 110

Leu Thr Asp Ile Arg Lys Leu Lys Asp Lys Tyr Tyr Lys Leu Gly Tyr
        115                 120                 125

Phe Asn Ala Asp Met Gly Phe Tyr Thr Tyr Lys Cys Leu Ser Thr Val
    130                 135                 140

Ser Ile Phe Ala Leu Ser Val Thr Ile Leu Tyr Asn Phe Ser Ser Ser
145                 150                 155                 160

Trp Phe Gly Ile Ile Pro Ser Ala Met Ile Met Gly Leu Phe Trp Gln
                165                 170                 175

Gln Cys Gly Trp Leu Ser His Asp Phe Leu His Gln Val Ser Asp
            180                 185                 190

Asn Arg Asp Ile Asn Asn Ala Ile Gly Gly Leu Phe Tyr Gly Ala Val
        195                 200                 205

Cys Gln Gly Phe Ser Met Ser Trp Trp Lys Asp Lys His Asn Thr His
    210                 215                 220

His Ala Ala Pro Asn Val Tyr Asn Glu Asp Pro Asp Ile Asp Thr His
225                 230                 235                 240

Pro Phe Leu Ala Trp Ser Glu Gln Ala Met Glu Leu Tyr Ala Asp Leu
                245                 250                 255

Asn Asp Gln Glu Met Ser Ser Arg Met Lys Lys Phe Met Leu Thr Asn
            260                 265                 270

Gln Ala Ile Ile Tyr Phe Pro Leu Leu Thr Phe Ala Arg Leu Ser Trp
```

```
                 275                 280                 285
Cys Thr Tyr Ser Leu Trp Phe Cys Phe Ser Arg Gly Thr Leu Ser Asn
            290                 295                 300

Pro Asn Lys Ile Pro Ile Asn Ile Glu Phe Ser Glu Lys Ala Ala Leu
305                 310                 315                 320

Leu Thr His Trp Phe Ile Thr Leu Ser Ile Thr Val Phe Met Pro Ser
                325                 330                 335

Thr Trp Ile Gln Ser Leu Val Phe Phe Ile Val Cys Gln Ala Ser Cys
            340                 345                 350

Gly Val Leu Leu Ala Ser Val Phe Ser Leu Asn His Asn Gly Met Ala
                355                 360                 365

Val Ile Ser Thr Glu Glu Ala Asp Asn Met Asp Phe Tyr Thr Lys Gln
370                 375                 380

Val Ile Thr Gly Arg Asp Val Thr Pro Ser His Phe Ile Gln Trp Phe
385                 390                 395                 400

Cys Gly Gly Leu Asn Tyr Gln Val Glu His His Leu Phe Pro Ala Leu
                405                 410                 415

Pro Arg His Ser Leu Pro Lys Val Gln Ala Asp Ile Glu Ala Leu Cys
                420                 425                 430

Lys Lys His Gly Ile Pro Tyr His Met Thr Gly Phe Ile Asp Gly Thr
            435                 440                 445

Lys Glu Val Leu Asp Arg Leu Gln Lys Ile Ala Thr Asn Ile Asn Asp
    450                 455                 460

Gln Ile
465

<210> SEQ ID NO 7
<211> LENGTH: 1371
<212> TYPE: DNA
<213> ORGANISM: Delacroixia coronatus

<400> SEQUENCE: 7
atgttaatag gcggcgttaa gttattcaga agaagcgaac tcaatactca cacctcttca      60
aaagatattc taaccagcaa ggtatacgct cccgcttata ccatcatcga taacaaagtc     120
tacgatgttc gcgacttcat tttagaccac cctggaggtc ccattatttt aacccatgtt     180
ggtagagatg gtactgatgc cttccacact ttccaccctg attcttcctg ggaaacccct     240
gccaattact atgttggaga tattcacccc gatgatgtta ttaatcaaga ttctaagcct     300 tccttttttaa ccgatataag aaagcttaag gataagtact ataagctcgg atacttcaat     360
gccgatatgg gttctatac ttacaagtgt ttatctactg tatccatttt tgccctctct     420
gttactatct tatataactt cagctctagt tggtttggta tcatccctc cgctatgatc     480 atgggcttat tttggcaaca atgtggctgg ttatctcacg atttcctcca tcatcaagtt     540
agcgacaata gagatatcaa taacgccatt ggtggtctct tctatggtgc cgtttgtcaa     600
ggtttctcta tgtcttggtg gaaagataag cacaataccc atcacgctgc cctaacgtt      660 tataacgaag accccgatat cgatacccac cccttttag cctggtccga caagctatg       720 gaactttatg ccgacttaaa tgaccaagaa atgtcttcta gaatgaagaa gttcatgctc     780
actaaccaag ctatcatcta cttcccctta ttgactttttg ctagattatc atggtgtacc    840
tacagtttat ggttctgctt ctctagagga actcttagca accccaacaa gatccccatt     900
aatattgaat tcagcgaaaa ggccgcttta ctcaccccatt ggttcattac cttatccatc    960
actgtcttca tgcctccac ttggattcaa tcccttgtat tctttattgt ttgtcaagcc    1020
```

```
tcttgtggtg tcctccttgc ctccgtattc tcccttaacc acaacggtat ggccgtaatc    1080
tccactgaag aagccgataa catggacttc tacaccaagc aagttattac tggtcgtgat    1140 gttacccccct ctcacttcat tcaatggttc tgtggaggct aaactacca agtagagcat    1200 cacttattcc ccgcccttcc tagacactct ctccctaaag ttcaagccga tattgaagcc    1260
ctctgcaaaa agcacggtat tccttaccat atgacaggct cattgatgg aactaaggag    1320 gtattagata gattgcaaaa aattgccacc aatatcaacg accaaattta a              1371
```

<210> SEQ ID NO 8
<211> LENGTH: 456
<212> TYPE: PRT
<213> ORGANISM: Delacroixia coronatus

<400> SEQUENCE: 8

```
Met Leu Ile Gly Gly Val Lys Leu Phe Arg Arg Ser Glu Leu Asn Thr
  1               5                  10                  15

His Thr Ser Ser Lys Asp Ile Leu Thr Ser Lys Val Tyr Ala Pro Ala
             20                  25                  30

Tyr Thr Ile Ile Asp Asn Lys Val Tyr Asp Val Arg Asp Phe Ile Leu
         35                  40                  45

Asp His Pro Gly Gly Pro Ile Ile Leu Thr His Val Gly Arg Asp Gly
     50                  55                  60

Thr Asp Ala Phe His Thr Phe His Pro Asp Ser Ser Trp Glu Thr Leu
 65                  70                  75                  80

Ala Asn Tyr Tyr Val Gly Asp Ile His Pro Asp Val Ile Asn Gln
                 85                  90                  95

Asp Ser Lys Pro Ser Phe Leu Thr Asp Ile Arg Lys Leu Lys Asp Lys
            100                 105                 110

Tyr Tyr Lys Leu Gly Tyr Phe Asn Ala Asp Met Gly Phe Tyr Thr Tyr
        115                 120                 125

Lys Cys Leu Ser Thr Val Ser Ile Phe Ala Leu Ser Val Thr Ile Leu
    130                 135                 140

Tyr Asn Phe Ser Ser Ser Trp Phe Gly Ile Ile Pro Ser Ala Met Ile
145                 150                 155                 160

Met Gly Leu Phe Trp Gln Gln Cys Gly Trp Leu Ser His Asp Phe Leu
                165                 170                 175

His His Gln Val Ser Asp Asn Arg Asp Ile Asn Asn Ala Ile Gly Gly
            180                 185                 190

Leu Phe Tyr Gly Ala Val Cys Gln Gly Phe Ser Met Ser Trp Trp Lys
        195                 200                 205

Asp Lys His Asn Thr His Ala Ala Pro Asn Val Tyr Asn Glu Asp
    210                 215                 220

Pro Asp Ile Asp Thr His Pro Phe Leu Ala Trp Ser Glu Gln Ala Met
225                 230                 235                 240

Glu Leu Tyr Ala Asp Leu Asn Asp Gln Glu Met Ser Ser Arg Met Lys
                245                 250                 255

Lys Phe Met Leu Thr Asn Gln Ala Ile Ile Tyr Phe Pro Leu Leu Thr
            260                 265                 270

Phe Ala Arg Leu Ser Trp Cys Thr Tyr Ser Leu Trp Phe Cys Phe Ser
        275                 280                 285

Arg Gly Thr Leu Ser Asn Pro Asn Lys Ile Pro Ile Asn Ile Glu Phe
    290                 295                 300

Ser Glu Lys Ala Ala Leu Leu Thr His Trp Phe Ile Thr Leu Ser Ile
```

-continued

```
                    305                 310                 315                 320
Thr Val Phe Met Pro Ser Thr Trp Ile Gln Ser Leu Val Phe Ile
                325                 330                 335
Val Cys Gln Ala Ser Cys Gly Val Leu Leu Ala Ser Val Phe Ser Leu
            340                 345                 350
Asn His Asn Gly Met Ala Val Ile Ser Thr Glu Glu Ala Asp Asn Met
            355                 360                 365
Asp Phe Tyr Thr Lys Gln Val Ile Thr Gly Arg Asp Val Thr Pro Ser
    370                 375                 380
His Phe Ile Gln Trp Phe Cys Gly Gly Leu Asn Tyr Gln Val Glu His
385                 390                 395                 400
His Leu Phe Pro Ala Leu Pro Arg His Ser Leu Pro Lys Val Gln Ala
                405                 410                 415
Asp Ile Glu Ala Leu Cys Lys Lys His Gly Ile Pro Tyr His Met Thr
            420                 425                 430
Gly Phe Ile Asp Gly Thr Lys Glu Val Leu Asp Arg Leu Gln Lys Ile
        435                 440                 445
Ala Thr Asn Ile Asn Asp Gln Ile
    450                 455

<210> SEQ ID NO 9
<211> LENGTH: 14
<212> TYPE: PRT
<213> ORGANISM: Artificial Sequence
<220> FEATURE:
<223> OTHER INFORMATION: Protein Motif 1

<400> SEQUENCE: 9

Val Tyr Asp Val Thr Glu Trp Val Lys Arg His Pro Gly Gly
1               5                   10

<210> SEQ ID NO 10
<211> LENGTH: 42
<212> TYPE: DNA
<213> ORGANISM: Artificial Sequence
<220> FEATURE:
<221> NAME/KEY: variation
<222> LOCATION: 1, 3, 6, 9, 12, 18, 24, 30, 33, 36, 39, 42
<223> OTHER INFORMATION: N= A,C,G,T; B=C,G,T; H=A,C,T; S=C,G; R=A,G;
      V=A,C,G; Y=C,T; D= A,T,C

<400> SEQUENCE: 10
gtbtaygayg tbaccgartg ggtbaagcgy cayccbgghg gh                             42

<210> SEQ ID NO 11
<211> LENGTH: 15
<212> TYPE: PRT
<213> ORGANISM: Artificial Sequence
<220> FEATURE:
<223> OTHER INFORMATION: Primer

<400> SEQUENCE: 11

Gly Ala Ser Ala Asn Trp Trp Lys His Gln His Asn Val His His
1               5                   10                  15

<210> SEQ ID NO 12
<211> LENGTH: 45
<212> TYPE: DNA
<213> ORGANISM: Artificial Sequence
<220> FEATURE:
<221> NAME/KEY: variation
<222> LOCATION: 3, 6, 12, 27, 33, 39, 42, 45
<223> OTHER INFORMATION: N= A,C,G,T; B=C,G,T; H=A,C,T; S=C,G; R=A,G;
```

V=A,C,G; Y=C,T; D= A,T,C

<400> SEQUENCE: 12
gghgcytccg cyaactggtg gaagcaycag cayaacgtbc aycay                45

<210> SEQ ID NO 13
<211> LENGTH: 45
<212> TYPE: DNA
<213> ORGANISM: Artificial Sequence
<220> FEATURE:
<221> NAME/KEY: variation
<222> LOCATION: 1, 4, 7, 13, 19, 34, 40, 43
<223> OTHER INFORMATION: N= A,C,G,T; B=C,G,T; H=A,C,T; S=C,G; R=A,G;
    V=A,C,G; Y=C,T; D= A,T,C

<400> SEQUENCE: 13
rtgrtgvacg ttrtgctgrt gcttccacca gttrgcggar gcdcc                45

<210> SEQ ID NO 14
<211> LENGTH: 12
<212> TYPE: PRT
<213> ORGANISM: Artificial Sequence
<220> FEATURE:
<223> OTHER INFORMATION: Protein Motif 3

<400> SEQUENCE: 14

Asn Tyr Gln Ile Glu His His Leu Phe Pro Thr Met
 1               5                  10

<210> SEQ ID NO 15
<211> LENGTH: 36
<212> TYPE: DNA
<213> ORGANISM: Artificial Sequence
<220> FEATURE:
<221> NAME/KEY: variation
<222> LOCATION: 6, 12, 15, 18, 21, 24, 27, 30,
<223> OTHER INFORMATION: N = A,C,G,T; B=C,G,T; H=A,C,T; S=C,G; R=A,G;
    V=A,C,G; Y=C,T; D= A,T,C

<400> SEQUENCE: 15
ttgatrgtct arctygtrgt rgasaarggv tggtac                          36

<210> SEQ ID NO 16
<211> LENGTH: 13
<212> TYPE: PRT
<213> ORGANISM: Artificial Sequence
<220> FEATURE:
<221> NAME/KEY: VARIANT
<222> LOCATION: 2, 4, 6, 9, 11
<223> OTHER INFORMATION: Xaa = unknown or other

<400> SEQUENCE: 16

His Xaa His Xaa His Xaa His His Xaa His Xaa His His
 1               5                  10

<210> SEQ ID NO 17
<211> LENGTH: 24
<212> TYPE: DNA
<213> ORGANISM: Artificial Sequence
<220> FEATURE:
<221> NAME/KEY: variation
<222> LOCATION: 10, 13, 16, 18, 19, 22
<223> OTHER INFORMATION: N = A,C,G,T; B=C,G,T; H=A,C,T; S=C,G; R=A,G;
    V=A,C,G; Y=C,T; D= A,T,C

<400> SEQUENCE: 17
catcatcatn ggraanarrt grtg                                       24

<210> SEQ ID NO 18
<211> LENGTH: 30
<212> TYPE: DNA
<213> ORGANISM: Artificial Sequence
<220> FEATURE:
<221> NAME/KEY: variation
<222> LOCATION: 15, 18, 21, 24, 27, 30
<223> OTHER INFORMATION: N= A,C,G,T; B=C,G,T; H=A,C,T; S=C,G; R=A,G;
   V=A,C,G; Y=C,T; D= A,T,C

<400> SEQUENCE: 18
ctactactac tacaycayac ntayacnaay                                      30

<210> SEQ ID NO 19
<211> LENGTH: 28
<212> TYPE: DNA
<213> ORGANISM: Artificial Sequence
<220> FEATURE:
<223> OTHER INFORMATION: Primer RO1526

<400> SEQUENCE: 19
tgcctccgta ttctcccttā accacaac                                        28

<210> SEQ ID NO 20
<211> LENGTH: 30
<212> TYPE: DNA
<213> ORGANISM: Artificial Sequence
<220> FEATURE:
<223> OTHER INFORMATION: Primer RO1528

<400> SEQUENCE: 20
cttccacact ttccaccctg attcttcctg                                      30

<210> SEQ ID NO 21
<211> LENGTH: 24
<212> TYPE: DNA
<213> ORGANISM: Artificial Sequence
<220> FEATURE:
<223> OTHER INFORMATION: Prime primer

<400> SEQUENCE: 21
gctgtcaacg atacgctacg taac                                            24

<210> SEQ ID NO 22
<211> LENGTH: 28
<212> TYPE: DNA
<213> ORGANISM: Artificial Sequence
<220> FEATURE:
<223> OTHER INFORMATION: Primer RO1524

<400> SEQUENCE: 22
tgaatccaag tggagggcat gaagacag                                        28

<210> SEQ ID NO 23
<211> LENGTH: 30
<212> TYPE: DNA
<213> ORGANISM: Artificial Sequence
<220> FEATURE:
<223> OTHER INFORMATION: Primer RO1525

<400> SEQUENCE: 23
cggaggggat gataccaaac caactagagc                                      30

<210> SEQ ID NO 24
<211> LENGTH: 23
<212> TYPE: DNA

-continued

<213> ORGANISM: Artificial Sequence
<220> FEATURE:
<223> OTHER INFORMATION: Prime primer

<400> SEQUENCE: 24
cgactggagc acgaggacac tga                                                 23

<210> SEQ ID NO 25
<211> LENGTH: 26
<212> TYPE: DNA
<213> ORGANISM: Artificial Sequence
<220> FEATURE:
<223> OTHER INFORMATION: Prime primer

<400> SEQUENCE: 25
ggacactgac atggactgaa ggagta                                              26

<210> SEQ ID NO 26
<211> LENGTH: 23
<212> TYPE: DNA
<213> ORGANISM: Artificial Sequence
<220> FEATURE:
<223> OTHER INFORMATION: Prime primer

<400> SEQUENCE: 26
cgctacgtaa cggcatgaca gtg                                                 23

<210> SEQ ID NO 27
<211> LENGTH: 37
<212> TYPE: DNA
<213> ORGANISM: Artificial Sequence
<220> FEATURE:
<223> OTHER INFORMATION: Forward Primer

<400> SEQUENCE: 27
tttaaaatga atggtaataa aattgcggcg ataaaag                                  37

<210> SEQ ID NO 28
<211> LENGTH: 36
<212> TYPE: DNA
<213> ORGANISM: Artificial Sequence
<220> FEATURE:
<223> OTHER INFORMATION: Reverse primer

<400> SEQUENCE: 28
ctagctagct taaatttggt cgttgatatt ggtggc                                   36

<210> SEQ ID NO 29
<211> LENGTH: 33
<212> TYPE: DNA
<213> ORGANISM: Artificial Sequence
<220> FEATURE:
<223> OTHER INFORMATION: Forward Primer

<400> SEQUENCE: 29
tttaaaatga taaagaagg ggcaatatta acc                                       33

<210> SEQ ID NO 30
<211> LENGTH: 36
<212> TYPE: DNA
<213> ORGANISM: Artificial Sequence
<220> FEATURE:
<223> OTHER INFORMATION: Reverse Primer

<400> SEQUENCE: 30
ctagctagct taaatttggt cgttgatatt ggtggc                                   36

```
<210> SEQ ID NO 31
<211> LENGTH: 33
<212> TYPE: DNA
<213> ORGANISM: Artificial Sequence
<220> FEATURE:
<223> OTHER INFORMATION: Primer RO1585

<400> SEQUENCE: 31
aaaggatcca atatgttaat aggcggcgtt aag                                    33

<210> SEQ ID NO 32
<211> LENGTH: 34
<212> TYPE: DNA
<213> ORGANISM: Artificial Sequence
<220> FEATURE:
<223> OTHER INFORMATION: Primer RO1584

<400> SEQUENCE: 32
atcctcgagt taaatttggt cgttgatatt ggtg                                   34

<210> SEQ ID NO 33
<211> LENGTH: 5
<212> TYPE: PRT
<213> ORGANISM: Artificial Sequence
<220> FEATURE:
<223> OTHER INFORMATION: PRDC12; Histidine Box 1

<400> SEQUENCE: 33

His Asp Phe Leu His
 1               5

<210> SEQ ID NO 34
<211> LENGTH: 5
<212> TYPE: PRT
<213> ORGANISM: Artificial Sequence
<220> FEATURE:
<223> OTHER INFORMATION: PRDC12; Histidine Box 2

<400> SEQUENCE: 34

His Asn Thr His His
 1               5

<210> SEQ ID NO 35
<211> LENGTH: 5
<212> TYPE: PRT
<213> ORGANISM: Artificial Sequence
<220> FEATURE:
<223> OTHER INFORMATION: PRDC12; Histidine Box 3

<400> SEQUENCE: 35

Gln Val Glu His His
 1               5

<210> SEQ ID NO 36
<211> LENGTH: 4
<212> TYPE: PRT
<213> ORGANISM: Artificial Sequence
<220> FEATURE:
<223> OTHER INFORMATION: PRDC12; Histidine Box

<400> SEQUENCE: 36

His Pro Gly Gly
 1

<210> SEQ ID NO 37
```

<211> LENGTH: 477
<212> TYPE: PRT
<213> ORGANISM: Phaeodactylum tricornatum

<400> SEQUENCE: 37

```
Met Gly Lys Gly Gly Asp Ala Arg Ala Ser Lys Gly Ser Thr Ala Ala
 1               5                  10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Cys Ala Leu Val
130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Trp Lys Asn Lys
        195                 200                 205

His Asn Gly His His Ala Val Pro Asn Leu His Cys Ser Ser Ala Val
    210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
        275                 280                 285

Lys Cys Ala Phe Gly Leu Ala Ala Ser Glu Asn Ala Ala Leu Glu
    290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Tyr Phe Leu Thr Ala Thr Ala Ser
            340                 345                 350

Cys Gly Phe Leu Leu Ala Ile Val Phe Gly Leu Gly His Asn Gly Met
        355                 360                 365

Ala Thr Tyr Asn Ala Asp Ala Arg Pro Asp Phe Trp Lys Leu Gln Val
    370                 375                 380

Thr Thr Thr Arg Asn Val Thr Gly Gly His Gly Phe Pro Gln Ala Phe
```

```
                385                 390                 395                 400
Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
                420                 425                 430

Glu Ser Phe Cys Lys Glu Trp Gly Val Gln Tyr His Glu Ala Asp Leu
                435                 440                 445

Val Asp Gly Thr Met Glu Val Leu His His Leu Gly Ser Val Ala Gly
                450                 455                 460

Glu Phe Val Val Asp Phe Val Arg Asp Gly Pro Ala Met
465                 470                 475

<210> SEQ ID NO 38
<211> LENGTH: 458
<212> TYPE: PRT
<213> ORGANISM: Rhizopus oryzae

<400> SEQUENCE: 38

Met Ser Thr Ser Asp Arg Gln Ser Val Phe Thr Leu Lys Glu Leu Glu
  1               5                  10                  15

Leu Ile Asn Gln Lys His Arg Asp Gly Asp Lys Ser Ala Met Lys Phe
                 20                  25                  30

Ile Ile Ile Asp Arg Lys Val Tyr Asp Val Thr Glu Phe Leu Glu Asp
             35                  40                  45

His Pro Gly Gly Ala Gln Val Leu Leu Thr His Val Gly Lys Asp Ala
         50                  55                  60

Ser Asp Val Phe His Ala Met His Pro Glu Ser Ala Tyr Glu Ile Leu
65                  70                  75                  80

Asn Asn Tyr Phe Val Gly Asp Val Lys Asp Ala His Val Lys Glu Thr
                 85                  90                  95

Pro Ser Ala Gln Phe Ala Ser Glu Met Arg Gln Leu Arg Asp Gln Leu
                100                 105                 110

Lys Lys Glu Gly Tyr Phe His Ser Ser Lys Ala Tyr Tyr Val Tyr Lys
            115                 120                 125

Val Leu Ser Thr Leu Ala Leu Cys Ala Ala Gly Leu Thr Leu Leu Tyr
        130                 135                 140

Ala Tyr Gly His Thr Ser Thr Leu Ala Val Val Ala Ser Ala Ile Ile
145                 150                 155                 160

Val Gly Ile Phe Trp Gln Gln Cys Gly Trp Leu Ala His Asp Phe Gly
                165                 170                 175

His His Gln Cys Phe Glu Asp Arg Ser Trp Asn Asp Val Leu Val Val
            180                 185                 190

Phe Leu Gly Asn Phe Cys Gln Gly Phe Ser Leu Ser Trp Trp Lys Asn
        195                 200                 205

Lys His Asn Thr His His Ala Ser Thr Asn Val His Gly His Asp Pro
    210                 215                 220

Asp Ile Asp Thr Ala Pro Val Leu Leu Trp Asp Glu Tyr Ala Ser Ala
225                 230                 235                 240

Ala Tyr Tyr Ala Ser Leu Asp Glu Glu Pro Thr Met Ile Ser Arg Phe
                245                 250                 255

Leu Ala Glu Ser Val Leu Pro His Gln Thr Arg Tyr Tyr Phe Phe Val
            260                 265                 270

Leu Gly Phe Ala Arg Leu Ser Trp Ala Ile Gln Ser Leu Leu Tyr Ser
        275                 280                 285
```

```
Phe Lys Gln Gly Ala Ile Asn Lys Ser His Gln Leu Asn Leu Phe Glu
    290                 295                 300
Arg Phe Cys Leu Val Ser His Trp Thr Leu Phe Thr Tyr Cys Thr Leu
305                 310                 315                 320
Ala Trp Cys Ser Asn Val Tyr His Met Ile Leu Phe Phe Leu Val Ser
                    325                 330                 335
Gln Ala Thr Thr Gly Tyr Thr Leu Ala Leu Val Phe Ala Leu Asn His
                340                 345                 350
Asn Gly Met Pro Val Ile Thr Glu Glu Lys Ala Glu Ser Met Glu Phe
            355                 360                 365
Phe Glu Ile Gln Val Ile Thr Gly Arg Asp Val Thr Leu Ser Pro Leu
370                 375                 380
Gly Asp Trp Phe Met Gly Leu Asn Tyr Gln Ile Glu His His Val
385                 390                 395                 400
Phe Pro Asn Met Pro Arg His Asn Leu Pro Lys Val Lys Pro Met Val
                405                 410                 415
Lys Ser Leu Cys Lys Lys Tyr Asp Ile Asn Tyr His Asp Thr Gly Phe
                420                 425                 430
Leu Lys Gly Thr Leu Glu Val Leu Lys Thr Leu Asp Ile Thr Ser Lys
            435                 440                 445
Leu Ser Leu Gln Leu Ser Lys Lys Ser Phe
    450                 455

<210> SEQ ID NO 39
<211> LENGTH: 459
<212> TYPE: PRT
<213> ORGANISM: Pythium irregulare

<400> SEQUENCE: 39

Met Val Asp Leu Lys Pro Gly Val Lys Arg Leu Val Ser Trp Lys Glu
1               5                   10                  15
Ile Arg Glu His Ala Thr Pro Ala Thr Ala Trp Ile Val Ile His His
                20                  25                  30
Lys Val Tyr Asp Ile Ser Lys Trp Asp Ser His Pro Gly Gly Ser Val
            35                  40                  45
Met Leu Thr Gln Ala Gly Glu Asp Ala Thr Asp Ala Phe Ala Val Phe
        50                  55                  60
His Pro Ser Ser Ala Leu Lys Leu Leu Glu Gln Phe Tyr Val Gly Asp
65                  70                  75                  80
Val Asp Glu Thr Ser Lys Ala Glu Ile Glu Gly Glu Pro Ala Ser Asp
                85                  90                  95
Glu Glu Arg Ala Arg Arg Glu Arg Ile Asn Glu Phe Ile Ala Ser Tyr
            100                 105                 110
Arg Arg Leu Arg Val Lys Val Lys Gly Met Gly Leu Tyr Asp Ala Ser
        115                 120                 125
Ala Leu Tyr Tyr Ala Trp Lys Leu Val Ser Thr Phe Gly Ile Ala Val
    130                 135                 140
Leu Ser Met Ala Ile Cys Phe Phe Asn Ser Phe Ala Met Tyr Met
145                 150                 155                 160
Val Ala Gly Val Ile Met Gly Leu Phe Tyr Gln Gln Ser Gly Trp Leu
                165                 170                 175
Ala His Asp Phe Leu His Asn Gln Val Cys Glu Asn Arg Thr Leu Gly
            180                 185                 190
Asn Leu Ile Gly Cys Leu Val Gly Asn Ala Trp Gln Gly Phe Ser Val
        195                 200                 205
```

```
Gln Trp Trp Lys Asn Lys His Asn Leu His His Ala Val Pro Asn Leu
    210                 215                 220
His Ser Ala Lys Asp Glu Gly Phe Ile Gly Asp Pro Asp Ile Asp Thr
225                 230                 235                 240
Met Pro Leu Leu Ala Trp Ser Lys Glu Met Ala Arg Lys Ala Phe Glu
                245                 250                 255
Ser Ala His Gly Pro Phe Phe Ile Arg Asn Gln Ala Phe Leu Tyr Phe
            260                 265                 270
Pro Leu Leu Leu Ala Arg Leu Ser Trp Leu Ala Gln Ser Phe Phe
        275                 280                 285
Tyr Val Phe Thr Glu Phe Ser Phe Gly Ile Phe Asp Lys Val Glu Phe
    290                 295                 300
Asp Gly Pro Glu Lys Ala Gly Leu Ile Val His Tyr Ile Trp Gln Leu
305                 310                 315                 320
Ala Ile Pro Tyr Phe Cys Asn Met Ser Leu Phe Glu Gly Val Ala Tyr
                325                 330                 335
Phe Leu Met Gly Gln Ala Ser Cys Gly Leu Leu Leu Ala Leu Val Phe
            340                 345                 350
Ser Ile Gly His Asn Gly Met Ser Val Tyr Glu Arg Glu Thr Lys Pro
        355                 360                 365
Asp Phe Trp Gln Leu Gln Val Thr Thr Thr Arg Asn Ile Arg Ala Ser
    370                 375                 380
Val Phe Met Asp Trp Phe Thr Gly Gly Leu Asn Tyr Gln Ile Asp His
385                 390                 395                 400
His Leu Phe Pro Leu Val Pro Arg His Asn Leu Pro Lys Val Asn Val
                405                 410                 415
Leu Ile Lys Ser Leu Cys Lys Glu Phe Asp Ile Pro Phe His Glu Thr
            420                 425                 430
Gly Phe Trp Glu Gly Ile Tyr Glu Val Val Asp His Leu Ala Asp Ile
        435                 440                 445
Ser Lys Glu Phe Ile Thr Glu Phe Pro Ala Met
    450                 455

<210> SEQ ID NO 40
<211> LENGTH: 457
<212> TYPE: PRT
<213> ORGANISM: Mortierella alpina

<400> SEQUENCE: 40

Met Ala Ala Ala Pro Ser Val Arg Thr Phe Thr Arg Ala Glu Ile Leu
1               5                   10                  15
Asn Ala Glu Ala Leu Asn Glu Gly Lys Lys Asp Ala Glu Ala Pro Phe
            20                  25                  30
Leu Met Ile Ile Asp Asn Lys Val Tyr Asp Val Arg Glu Phe Val Pro
        35                  40                  45
Asp His Pro Gly Gly Ser Val Ile Leu Thr His Val Gly Lys Asp Gly
    50                  55                  60
Thr Asp Val Phe Asp Thr Phe His Pro Glu Ala Ala Trp Glu Thr Leu
65                  70                  75                  80
Ala Asn Phe Tyr Val Gly Asp Ile Asp Glu Ser Asp Arg Ala Ile Lys
                85                  90                  95
Asn Asp Asp Phe Ala Ala Glu Val Arg Lys Leu Arg Thr Leu Phe Gln
            100                 105                 110
Ser Leu Gly Tyr Tyr Asp Ser Ser Lys Ala Tyr Tyr Ala Phe Lys Val
```

-continued

```
                115                 120                 125
Ser Phe Asn Leu Cys Ile Trp Gly Leu Ser Thr Phe Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
            165                 170                 175

His Gln Val Phe Gln Asp Arg Phe Trp Gly Asp Leu Phe Gly Ala Phe
        180                 185                 190

Leu Gly Gly Val Cys Gln Gly Phe Ser Ser Ser Trp Trp Lys Asp Lys
            195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
            245                 250                 255

Met Val Leu Asn Gln Thr Trp Phe Tyr Phe Pro Ile Leu Ser Phe Ala
        260                 265                 270

Arg Leu Ser Trp Cys Leu Gln Ser Ile Met Phe Val Leu Pro Asn Gly
            275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
            325                 330                 335

Gln Ala Val Cys Gly Asn Leu Leu Ala Ile Val Phe Ser Leu Asn His
        340                 345                 350

Asn Gly Met Pro Val Ile Ser Lys Glu Glu Ala Val Asp Met Asp Phe
    355                 360                 365

Phe Thr Lys Gln Ile Ile Thr Gly Arg Asp Val His Pro Gly Leu Phe
370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
            405                 410                 415

Glu Thr Leu Cys Lys Lys Tyr Gly Val Arg Tyr His Thr Thr Gly Met
        420                 425                 430

Ile Glu Gly Thr Ala Glu Val Phe Ser Arg Leu Asn Glu Val Ser Lys
            435                 440                 445

Ala Ala Ser Lys Met Gly Lys Ala Gln
    450                 455
```

<210> SEQ ID NO 41
<211> LENGTH: 23
<212> TYPE: PRT
<213> ORGANISM: Delacroixia coronatus
<220> FEATURE:
<221> NAME/KEY: VARIANT
<222> LOCATION: 7
<223> OTHER INFORMATION: Xaa = Met or Ala

<400> SEQUENCE: 41

```
Met Asn Gly Asn Lys Ile Xaa Ala Ile Lys Glu Gly Ala Ile Leu Thr
1               5                   10                  15
```

-continued

Phe Ile Leu Ile Gly Gly Val
            20

<210> SEQ ID NO 42
<211> LENGTH: 23
<212> TYPE: PRT
<213> ORGANISM: Delacroixia coronatus

<400> SEQUENCE: 42

Met Asn Gly Asn Lys Ile Ala Ala Ile Lys Glu Gly Ala Ile Leu Thr
1               5                   10                  15

Phe Ile Leu Ile Gly Gly Val
            20

<210> SEQ ID NO 43
<211> LENGTH: 17
<212> TYPE: PRT
<213> ORGANISM: Delacroixia coronatus

<400> SEQUENCE: 43

Met Ala Ile Lys Glu Gly Ala Ile Leu Thr Phe Ile Leu Ile Gly Gly
1               5                   10                  15

Val

<210> SEQ ID NO 44
<211> LENGTH: 6
<212> TYPE: PRT
<213> ORGANISM: Delacroixia coronatus

<400> SEQUENCE: 44

Met Leu Ile Gly Gly Val
1               5

<210> SEQ ID NO 45
<211> LENGTH: 467
<212> TYPE: PRT
<213> ORGANISM: Mucor circinelloides

<400> SEQUENCE: 45

Met Ser Ser Asp Val Gly Ala Thr Val Pro His Phe Tyr Thr Arg Ala
1               5                   10                  15

Glu Leu Ala Asp Ile His Gln Asp Val Leu Asp Lys Lys Pro Glu Ala
            20                  25                  30

Arg Lys Leu Ile Val Val Glu Asn Lys Val Tyr Asp Ile Thr Asp Phe
        35                  40                  45

Val Phe Asp His Pro Gly Gly Glu Arg Val Leu Leu Thr Gln Glu Gly
    50                  55                  60

Arg Asp Ala Thr Asp Val Phe His Glu Met His Pro Pro Ser Ala Tyr
65                  70                  75                  80

Glu Leu Leu Ala Asn Cys Tyr Val Gly Asp Cys Glu Pro Lys Leu Pro
                85                  90                  95

Ile Asp Ser Thr Asp Lys Lys Ala Leu Asn Ser Ala Ala Phe Ala Gln
            100                 105                 110

Glu Ile Arg Asp Leu Arg Asp Lys Leu Glu Lys Gln Gly Tyr Phe Asp
        115                 120                 125

Ala Ser Thr Gly Phe Tyr Ile Tyr Lys Val Ser Thr Thr Leu Leu Val
    130                 135                 140

Cys Ile Val Gly Leu Ala Ile Leu Lys Ala Trp Gly Arg Glu Ser Thr
145                 150                 155                 160

-continued

```
Leu Ala Val Phe Ile Ala Ala Ser Leu Val Gly Leu Phe Trp Gln Gln
                165             170             175
Cys Gly Trp Leu Ala His Asp Tyr Ala His Tyr Gln Val Ile Lys Asp
            180             185             190
Pro Asn Val Asn Asn Leu Phe Leu Val Thr Phe Gly Asn Leu Val Gln
        195             200             205
Gly Phe Ser Leu Ser Trp Trp Lys Asn Lys His Asn Thr His His Ala
    210             215             220
Ser Thr Asn Val Ser Gly Glu Asp Pro Asp Ile Asp Thr Ala Pro Ile
225             230             235             240
Leu Leu Trp Asp Glu Phe Ala Val Ala Asn Phe Tyr Gly Ser Leu Lys
            245             250             255
Asp Asn Ala Ser Gly Phe Asp Arg Phe Ile Ala Glu His Ile Leu Pro
            260             265             270
Tyr Gln Thr Arg Tyr Tyr Phe Phe Ile Leu Gly Phe Ala Arg Thr Ser
            275             280             285
Trp Ala Ile Gln Ser Ile Ile Tyr Ser Phe Lys Asn Glu Thr Leu Asn
    290             295             300
Lys Ser Lys Leu Leu Ser Trp Cys Glu Arg Ile Phe Leu Ile Val His
305             310             315             320
Trp Val Phe Phe Thr Tyr Cys Thr Ile Ala Trp Ile Ser Ser Ile Arg
            325             330             335
Asn Ile Ala Met Phe Phe Val Val Ser Gln Ile Thr Thr Gly Tyr Leu
            340             345             350
Leu Ala Ile Val Phe Ala Met Asn His Asn Gly Met Pro Val Tyr Ser
            355             360             365
Pro Glu Glu Ala Asn His Thr Glu Phe Tyr Glu Leu Gln Cys Ile Thr
        370             375             380
Gly Arg Asp Val Asn Cys Thr Val Phe Gly Asp Trp Leu Met Gly Gly
385             390             395             400
Leu Asn Tyr Gln Ile Glu His His Leu Phe Pro Glu Met Pro Arg His
            405             410             415
His Leu Ser Lys Val Lys Ser Met Val Lys Pro Ile Ala Gln Lys Tyr
            420             425             430
Asn Ile Pro Tyr His Asp Thr Thr Val Ile Gly Gly Thr Ile Glu Val
            435             440             445
Leu Gln Thr Leu Asp Phe Val Gln Lys Ile Ser Gln Lys Phe Ser Lys
    450             455             460
Lys Met Leu
465
```